United States Patent [19]

Bodor

[11] Patent Number: 4,933,438
[45] Date of Patent: Jun. 12, 1990

[54] BRAIN-SPECIFIC ANALOGUES OF CENTRALLY ACTING AMINES

[75] Inventor: Nicholas S. Bodor, Gainesville, Fla.

[73] Assignee: University of Florida, Gainesville, Fla.

[21] Appl. No.: 208,872

[22] Filed: Jun. 20, 1988

Related U.S. Application Data

[60] Division of Ser. No. 785,903, Aug. 29, 1985, Pat. No. 4,771,059, which is a continuation-in-part of Ser. No. 584,800, Feb. 29, 1984, abandoned.

[51] Int. Cl.$^5$ .............................................. C07H 15/24
[52] U.S. Cl. ...................................... 536/6.4; 546/316
[58] Field of Search ............................ 536/6.4; 514/34

[56]  References Cited

U.S. PATENT DOCUMENTS 4,314,054 2/1982 Acton et al. .......................... 536/6.4
4,479,932 10/1984 Bodor ...................................... 424/9

FOREIGN PATENT DOCUMENTS 8303968 11/1983 PCT Int'l Appl. .
822351 10/1959 United Kingdom .

OTHER PUBLICATIONS

*Chemical Abstracts*, vol. 84, June 7, 1976, p. 447, abstract No. 164580z.
*Chemical Abstracts*, vol. 81, Aug. 5, 1974, p. 24, abstract No. 20899a.

*Primary Examiner*—Johnnie R. Brown
*Assistant Examiner*—Elli Peselev
*Attorney, Agent, or Firm*—Mary Katherine Baumeister; Dennis P. Clarke

[57] ABSTRACT

The subject compounds, which are adapted for the site-specific/sustained delivery of centrally acting drug species to the brain, are compounds of the formula

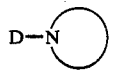

(I)

and the non-toxic pharmaceutically acceptable salts thereof, wherein D is the residue of a centrally acting primary, secondary or tertiary amine and

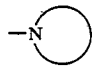

is an unsubstituted or substituted dihydropyridyl, dihydroquinolyl or dihydroisoquinolyl radical. The corresponding ionic pyridinium, quinolinium and isoquinolinium salts

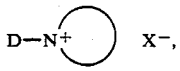

wherein $X^-$ is the anion of a non-toxic pharmaceutically acceptable acid, are also disclosed.

10 Claims, No Drawings

BRAIN-SPECIFIC ANALOGUES OF CENTRALLY ACTING AMINES

CROSS-REFERENCE TO RELATED APPLICATIONS

This application is a division of application Ser. No. 785,903, filed Aug. 29, 1985, now U.S. Pat. No. 4,771,059, which is a continuation-in-part of applicant's copending application Ser. No. 584,800, filed Feb. 29, 1984, now abandoned.

FIELD OF THE INVENTION

The present invention relates to new derivatives of centrally acting amines in which a primary, secondary or tertiary amine function has been replaced with a dihydropyridine/pyridinium salt redox system. The new dihydropyridine analogues are a delivery system for the corresponding new quaternary compounds, which are pharmacologically active in vivo and are characterized by site-specific and sustained delivery to the brain.

BACKGROUND OF THE INVENTION

The delivery of drug species to the brain is oftimes seriously limited by transport and metabolism factors and, more specifically, by the functional barrier of the endothelial brain capillary wall, i.e. the blood-brain barrier or BBB. Site-specific delivery and sustained delivery of drugs to the brain are even more difficult.

Indeed, the barriers separating plasma from the brain and cerebrospinal fluid (CSF) are complex systems involving passive and active transport and subserve a number of important functions. The boundary between plasma and the central nervous system (CNS) is much less permeable than that between plasma and other tissue cells to a variety of water soluble substances, such as organic electrolytes, organic acids and bases, as well as to large molecules such as proteins. Such a barrier also provides a path for clearance from the brain of breakdown products of cellular metabolism. The CNS and its fluids can be considered basically a three-compartment system: the blood or the plasma, CSF and brain tissue. There is a diffusion-controlled exchange between CSF and the extracellular fluid (CF) of the brain. It has also been suggested that the permeabilities of blood-CSF and blood-brain barriers are practically identical with respect to drugs and other foreign substances. Mayer et al, *J. Pharmacol. and Exp. Therap.*, 125, 185 (1959).

The BBB is, moreover, basically the result of the fact that the endothelial cells in the brain capillaries are joined by continuous, tight intercellular junctions, such that material has to pass through the cells rather than between them in order to move from blood to brain. It is interesting that there are areas within the brain, such as the subfornical body and the postremia, in which the capillary cells are not closely linked so that they lack the characteristics of the BBB. They provide the entry of small amounts of compounds which would not ordinarily enter the barriers. Hoffman and Olszewzki, *Neurology* (Minneap.), 11, 1081 (1961).

Foreign compounds which enter organs other than the central nervous system with ease, may penetrate the CNS slowly or hardly at all. A number of theories concerning the nature of the barrier have been proposed. The widely accepted concept describes the boundary as a fat-like layer interspersed with small pores, although the BBB is not a simple, anatomically well-defined unitary physical entity. Shuttleworth, *Prog. Exp. Tumor Res.*, 17, 279 (1972). Penetration of such a barrier may occur by several processes: lipid soluble substances may passively penetrate into the cells, while small molecules such as water and urea may pass through the pores. In addition to these simple physical processes, carrier-mediated and active transport processes govern the movement of many molecules through the BBB. Thus, it is generally accepted that lipid solubility, degree of ionic dissociation or protonation and the ability of temporary combination with membrane constituents affect delivery through the BBB. It has been shown, for example, that in the class of barbiturates, a quantitative correlation could be established between their ease to pass into the brain (as reflected by the different times of onset of anesthetic action) and their lipid/water partition coefficient. Mark et al, *J. Pharmacol. and Exp. Therap.*, 123, 79 (1957). The role of lipid solubility in drug penetration through the BBB is also exemplified by the better absorption of the sparingly water-soluble thiamine propyl disulfide (TPD) as compared to the water-soluble thiamine hydrochloride (THCl). Thomson et al, *Ann. Int. Med.*, 74, 529 (1971). Some materials such as glucose and amino acids are transported by active mechanism, characterized by saturation, bidirectional molecular specificity, bi-directional competitive inhibition and bidirectional countertransport. Fishman, *Am. J. Physiol.*, 206, 836 (1964).

Changes in permeability of the BBB can be caused by several pathological and toxicological processes. Pardridge, Connor and Crawford, *CRC Crit. Rev. Toxicol.*, 179 (1975). A general increase in the barrier permeability, such as a nonspecific breakdown of the barrier has, however, several consequences, including cerebral edema.

It too is well documented that the BBB is relatively impermeable to the ionized forms of drugs and other molecules. Drugs which are weak organic electrolytes appear to pass from blood to CSF to reach a steady state ratio characteristic of each molecule according to its $pk_a$ and the existence of a normal pH gradient between blood and CSF. It is clear that it is the most difficult for quaternary pyridinium or ammonium salts to penetrate the BBB.

And removal of substances from the brain and CSF is obviously a significant factor in regulating drug concentrations in the CNS. There are several efflux processes: bulk flow via the arachnoid villi, diffusion of lipid soluble substances into brain and blood, active transport and metabolism by adjacent meninges. Once a drug or metabolite enters the CSF from blood or brain by simple diffusion, it may rapidly be removed, either by nonselective bulk flow or by active transport mechanism associated with the choroid plexus or other nondefined structures in the CSF compartment. It is generally accepted that highly lipid-soluble drugs leave the CSF more rapidly than poorly lipid-soluble ones, but the barrier to passage of compounds from CSF has only superficial similarity to the blood-CSF barrier.

Drug elimination processes from the brain are significantly directly related to drug accumulation in the brain. It is generally assumed that efflux in the opposite direction involves almost the same processes as for entry, except that the role of the bulk flow and the metabolic processes in the brain are not to be overlooked.

The two elimination processes studied in the earlier literature and which can be said to have a certain bearing on the present invention involve elimination from the brain of ionic species. Thus, it is found that non-metabolized ionic species, such as the acetate ion, have a three times slower elimination rate from the CSF than from the blood. Freundt, *Arz., Forsch.,* 23, 949 (1973). An even more dramatic change in the elimination rate was found in the case of a quaternary piperidinium salt. The quaternary salt, formed in situ after delivery of a haloalkylamine, which undergoes cyclization to the quaternary salt, in the brain, as well, was found to have an at least ten times slower elimination rate from the brain than from the rest of the body. It was concluded by the authors [Ross and Froden, *Eur. J. Pharmacol.,* 13, 46 (1970)] that the outflow rate of the quaternary salt corresponded to the inflow rate. Similar results were obtained for the erythrocytes: the efflux of the quaternary salt was very slow. Ross, *J. Pharm. Pharmacol.,* 27, 322 (1975).

A dihydropyridine⇌pyridinium redox system has now been successfully applied to delivery to the brain of a number of drugs. Generally speaking, according to this system, a dihydropyridine derivative of a biologically active compound is synthesized, which derivative can enter the CNS through the blood-brain barrier following its systemic administration. Subsequent oxidation of the dihydropyridine species to the corresponding pyridinium salt leads to delivery of the drug to the brain.

Two main approaches have been used thus far for delivering drugs to the brain using this redox system. The first approach involves derivation of selected drugs which contain a pyridinium nucleus as an integral structural component. This approach was first applied to delivering to the brain N-methylpyridinium-2-carbaldoxime chloride (2-PAM), the active nucleus of which constitutes a quaternary pyridinium salt, by way of the dihydropyridine latentiated prodrug form thereof.

Thus, a hydrophilic compound (2-PAM) was made lipoidal (i.e. lipophilic) by making its dihydropyridine form (Pro-2-PAM) to enable its penetration through lipoidal barriers. This simple prodrug approach allowed the compound to get into the brain as well as other organs, but this manipulation did not and could not result in any brain specificity. On the contrary, such approach was delimited to relatively small molecule quaternary pyridinium ring-containing drug species and did not provide the overall ideal result of brainspecific, sustained release of the desired drug, with concomitant rapid elimination from the general circulation, enhanced drug efficacy and decreased toxicity. No "trapping" in the brain of the 2-PAM formed in situ resulted, and obviously no brain-specific, sustained delivery occurred as any consequence thereof: the 2-PAM was eliminated as fast from the brain as it was from the general circulation and other organs. Compare U.S. Pat. Nos. 3,929,813 and 3,962,447; Bodor et al, *J. Pharm. Sci.,* 67, No. 5, 685 (1978). See also Bodor, "Novel Approaches for the Design of Membrane Transport Properties of Drugs", in *Design of Biopharmaceutical Properties Through Prodrugs and Analogs*, Roche, E. B. (ed.), APhA Academy of Pharmaceutical Sciences, Washington, D.C., 98–135 (1976). Subsequent extension of this first approach to delivering a much larger quaternary salt, berberine, to the brain via its dihydropyridine prodrug form was, however, found to provide site-specific sustained delivery to the brain of that anticancer agent. See Bodor et al, *Science,* Vol. 214, Dec. 18, 1981, pp. 1370–1372.

The second approach for delivering drugs to the brain using the redox system involves the use of a pyridinium carrier chemically linked to a biologically active compound. Bodor et al, *Science,* Vol. 214, Dec. 18, 1981, pp. 1370–1372, outlines a scheme for this specific and sustained delivery of drug species to the brain, as depicted in the following Scheme 1:

SCHEME 1: BBB, BLOOD-BRAIN BARRIER

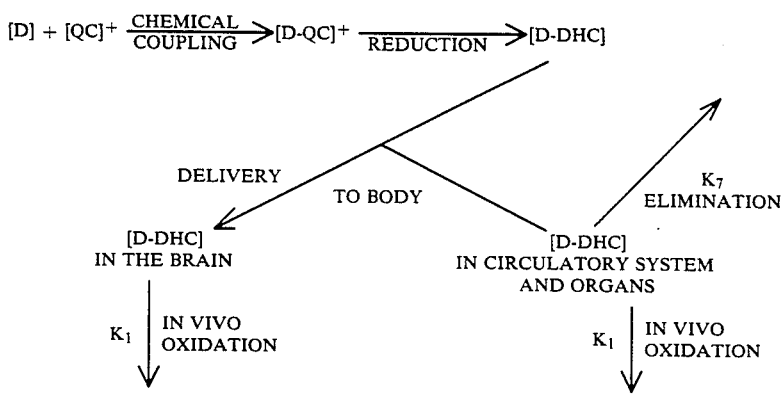

-continued
SCHEME 1: BBB, BLOOD-BRAIN BARRIER

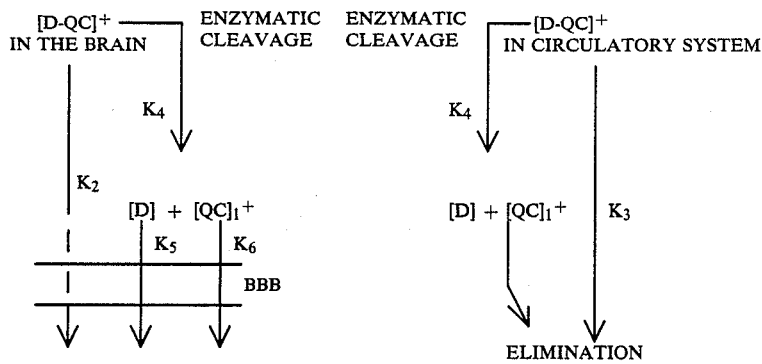

According to the scheme in *Science*, a drug [D] is coupled to a quaternary carrier [QC]+ and the [D-QC]+ which results is then reduced chemically to the lipoidal dihydro form [D-DHC]. After administration of [D-DHC] in vivo, it is rapidly distributed throughout the body, including the brain. The dihydro form [D-DHC] is then in situ oxidized (rate constant, $k_1$) (by the $NAD \rightleftharpoons NADH$ system) to the ideally inactive original [D-QC]+ quaternary salt which, because of its ionic, hydrophilic character, should be rapidly eliminated from the general circulation of the body, while the blood-brain barrier should prevent its elimination from the brain ($k_3 >> k_2$; $k_3 >> k_7$). Enzymatic cleavage of the [D-QC]+ that is "locked" in the brain effects a sustained delivery of the drug species [D], followed by its normal elimination ($k_5$), metabolism. A properly selected carrier [QC]+ will also be rapidly eliminated from the brain ($k_6 >> k_2$). Because of the facile elimination of [D-QC]+ from the general circulation, only minor amounts of drug are released in the body ($k_3 >> k_4$); [D] will be released primarily in the brain ($k_4 > k_2$). The overall result ideally will be a brain-specific sustained release of the target drug species. Specifically, Bodor et al worked with phenylethylamine as the drug model. That compound was coupled to nicotinic acid, then quaternized to give compounds of the formula

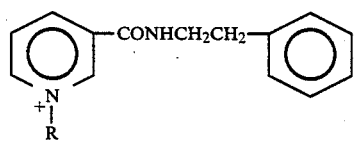

(R = CH$_3$ or CH$_2$—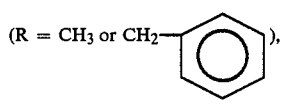), which were subsequently reduced by sodium dithionite to the corresponding compounds of the formula

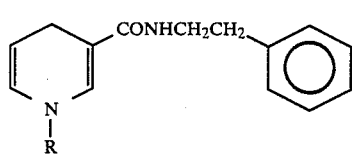

(R = CH$_3$ or CH$_2$—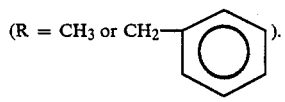).

Testing of the N-methyl derivative in vivo supported the criteria set forth in Scheme 1. Bodor et al speculated that various types of drugs might possibly be delivered using the depicted or analogous carrier systems and indicated that use of N-methylnicotinic acid esters and amides and their pyridine ring-substituted derivatives was being studied for delivery of amino- or hydroxyl-containing drugs, including small peptides, to the brain. No other possible specific carriers were disclosed. Other reports of this work with the redox carrier system have appeared in *The Friday Evening Post*, Aug. 14, 1981, Health Center Communications, University of Florida, Gainesville, Fl.; *Chemical & Engineering News*, Dec. 21, 1981, pp. 24–25; and *Science News*, Jan. 2, 1982, Vol. 121, No. 1, page 7. More recently, the redox carrier system has been substantially extended in terms of possible carriers and drugs to be delivered. See International Patent Application No. PCT/US83/00725, filed May 12, 1983 and published Nov. 24, 1983 under International Publication No. WO83/03968. Also see Bodor et al, *Pharmacology and Therapeutics*, Vol. 19, No. 3, pp. 337–386 (1983).

Nevertheless, serious need also exists in this art for new, centrally acting drugs which can be site-specifically and sustainedly delivered to the brain, while at the same time avoiding the aforesaid noted and notable disadvantages and drawbacks associated with penetration of the blood-brain barrier, with dihydropyridine latentiated prodrug forms of drug species themselves comprising a pyridinium salt active nucleus, with the necessity for introducing critically coordinated and designed, release rate-controlling substituents onto any particular drug carrier moiety, and/or with the limitation of delivery of only known drug entities.

SUMMARY AND OBJECTS OF THE INVENTION

Accordingly, a major object of the present invention is the provision of a new approach for delivering drugs to the brain using the redox system. This approach provides new derivatives of centrally acting amines in which a primary, secondary or tertiary amine function has been replaced with a dihydropyridine/pyridinium salt redox system. The new dihydropyridine analogues of the invention are characterized by the structual formula

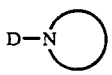  (I)

Wherein D is the residue of a centrally acting primary, secondary or tertiary amine, and

is a radical of the formula

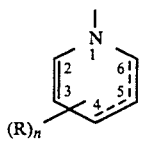  (a)

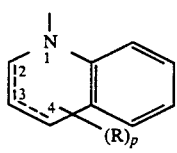  (b)

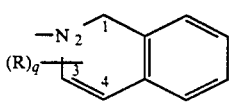  (c)

or

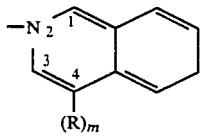  (d)

wherein the dotted line in formula (a) indicates the presence of a double bond in either the 4 or 5 position of the dihydropyridine ring; the dotted line in formula (b) indicates the presence of a double bond in either the 2 or 3 position of the dihydroquinoline ring system; m is zero or one; n is zero, one or two; p is zero, one or two, provided that when p is one or two, each R in formula (b) can be located on either of the two fused rings; q is zero, one, or two, provided that when q is one or two, each R in formula (c) can be located on either of the two fused rings; and each R is independently selected from the group consisting of halo, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is H or $C_1$-$C_7$ alkyl, and —CONR'R'' wherein R' and R'', which can be the same or different, are each H or $C_1$-$C_7$ alkyl. Preferably, n, m, p or q is one and R is located in the 3 position of the dihydropyridine ring, in the 3 position of the dihydroquinoline ring system or in the 4 position of the dihydroisoquinoline ring system. Most preferably, R is —$CONH_2$.

The nontoxic pharmaceutically acceptable salts of the compounds of formula (I) are also within the ambit of this invention.

The new dihydropyridine analogues of formula (I) act as a delivery system for the corresponding quaternary compounds in vivo; the quaternary derivatives, which also are chemical intermediates to the dihydro compounds, are pharmacologically active and are characterized by site-specific and sustained delivery to the brain when administered via the corresponding dihydropyridine form. The new quaternary salts are characterized by the structural formula

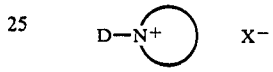  (II)

wherein D is defined as with formula (I), $X^-$ is the anion of a non-toxic pharmaceutically acceptable acid and

is a radical of the formula

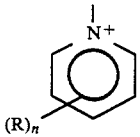  (a)

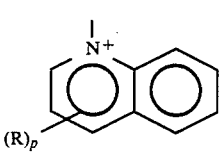  (b)

or

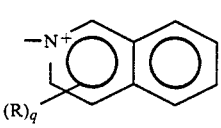  (c)

wherein n, p, q and R are defined as with formula (I).

Briefly then, the present invention features a dihydropyridine⇌pyridinium salt redox system for the specific and sustained delivery of a centrally acting drug to the brain according to the following Scheme 2:

SCHEME 2

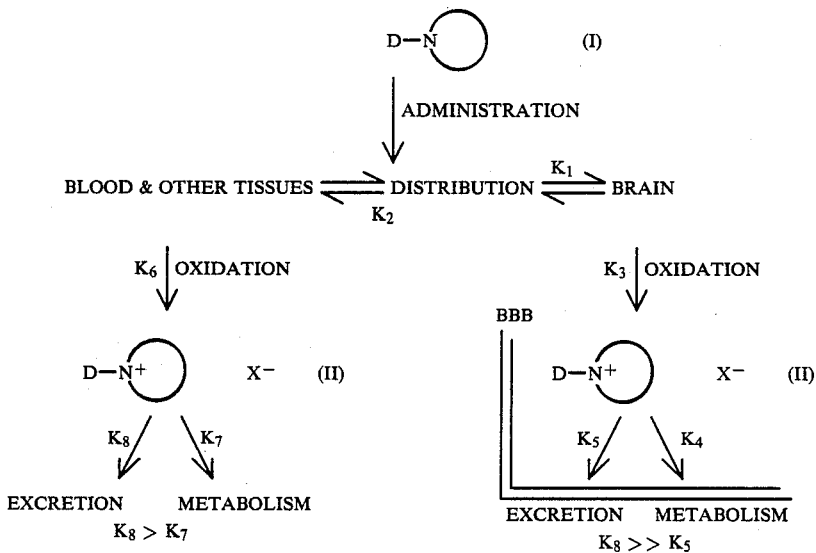

Scheme 2 shows the expected sequence of events following administration of a compound of formula (I). Due to its lipophilic nature, the dihydropyridine compound of formula (I) will distribute throughout the body and has easy access to the brain through the blood-brain barrier. Upon oxidation, which occurs throughout the body, the formula (I) compound will be converted to the corresponding quaternary of formula (II). The quaternary form will be "locked" preferentially in the brain, since it can be excreted easily peripherally, but cannot move readily through the BBB. Sustained levels of the formula (II) quaternary will be present at the site of action, the brain, resulting in longer duration of action.

DETAILED DESCRIPTION OF THE INVENTION

More particularly in accord with the present invention, the following definitions are applicable:

The term "lipoidal" as used herein is intended to mean lipid-soluble or lipophilic.

The term "halo" encompasses fluoro, chloro, bromo and iodo.

The term "$C_1$-$C_7$ alkyl" includes straight and branched lower alkyl radicals having up to seven carbon atoms. When R, R', R'', and/or R''' are $C_1$-$C_7$ alkyl, they are preferably methyl or ethyl.

The term "$C_1$-$C_7$ alkoxy" includes straight and branched chain lower alkoxy radicals having up to seven carbon atoms. When R is $C_1$-$C_7$ alkoxy, it is preferably methoxy or ethoxy.

The term "$C_2$-$C_8$ alkoxycarbonyl" designates straight and branched chain radicals of the formula $$(C_1\text{-}C_7 \text{ alkyl}) -O-\overset{\overset{\displaystyle O}{\|}}{C}-$$

wherein the $C_1$-$C_7$ alkyl group is defined as above. When R is alkoxycarbonyl, it is preferably ethoxycarbonyl or isopropoxycarbonyl.

The term "$C_2$-$C_8$ alkanoyloxy" designates straight and branched chain radicals of the formula $$(C_1\text{-}C_7 \text{ alkyl}) -\overset{\overset{\displaystyle O}{\|}}{C}-O-$$

wherein the $C_1$-$C_7$ alkyl group is defined as above. When R is alkanoyloxy it is preferably acetoxy, pivalyloxy or isobutryloxy.

The term "$C_1$-$C_7$ haloalkyl" designates straight and branched chain lower alkyl radicals having up to seven carbon atoms and bearing one or more halo substituents (F, Cl, Br or I), which can be the same or different. Preferably, when R is haloalkyl, the group contains 1 or 2 carbon atoms and bears 1 to 3 halogen substituents, e.g. chloromethyl or trifluoromethyl.

The term "$C_1$-$C_7$ alkylthio" includes straight and branched chain radicals of the type $$(C_1\text{-}C_7 \text{ alkyl})-S-$$

wherein $C_1$-$C_7$ alkyl is defined as before. When R is alkylthio, it is preferably methylthio.

The terms "$C_1$-$C_7$ alkylsulfinyl" and "$C_1$-$C_7$ alkylsulfonyl" designate radicals of the formulas $$(C_1\text{-}C_7 \text{ alkyl})-SO-$$

and
$$(C_1\text{-}C_7 \text{ alkyl})-SO_2-,$$

respectively, wherein $C_1$-$C_7$ alkyl is defined as before. When R is alkylsulfinyl or alkylsulfonyl, methylsulfinyl and methylsulfonyl are preferred.

When R is —CH=NOR''', it is preferably —CH=NOH

When R is —CONR'R'', it is preferably —CONH$_2$ or —CON(CH$_3$)$_2$.

The expression "hydroxyl protective group" as used hereinbelow is intended to designate a group which is inserted in place of the hydrogen atom(s) of an OH group or groups in order to prevent premature metabolism of said OH group or groups prior to the compound's reaching the desired site in the body. Typical hydroxyl protective groups contemplated by the present invention are acyl groups and carbonates.

When the hydroxyl protective group is acyl (i.e., when it is an organic radical derived from a carboxylic acid by removal of the hydroxyl group), it preferably represents an acyl radical selected from the group consisting of alkanoyl having 2 to 8 carbon atoms; alkenoyl having one or two double bonds and 3 to 8 carbon atoms;

wherein the cycloalkyl portion contains 3 to 7 ring atoms and r is zero, one, two or three; phenoxyacetyl; pyridinecarbonyl; and

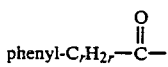

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms.

When the acyl group is alkanoyl, there are included both unbranched and branched alkanoyl, for example, acetyl, propionyl, butyryl, isobutyryl, valeryl, isovaleryl, 2-methylbutanoyl, pivalyl (pivaloyl), 3-methylpentanoyl, 3,3-dimethylbutanoyl, 2,2-dimethylpentanoyl and the like. Pivalyl, isobutyryl and isovaleryl are especially preferred.

When the acyl group is alkenoyl, there are included, for example, crotonyl, 2,5-hexadienoyl and 3,6-octadienoyl.

When the acyl group is

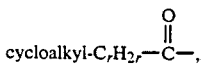

there are included cycloalkanecarbonyl and cycloalkanealkanoyl groups wherein the cycloalkane portion can optionally bear 1 or 2 alkyl groups as substituents, e.g. cyclopropanecarbonyl, 1-methylcyclopropanecarbonyl, cyclopropaneacetyl, α-methylcyclopropaneacetyl, 1-methylcylopropaneacetyl, cyclopropanepropionyl, α-methylcyclopropanepropionyl, 2-isobutylcyclopropanepropionyl, cyclobutanecarbonyl, 3,3-dimethylcyclobutanecarbonyl, cyclobutaneacetyl, 2,2-dimethyl-3-ethylcyclobutaneacetyl, cyclopentanecarbonyl, cyclohexaneacetyl, cyclohexanecarbonyl, cycloheptanecarbonyl and cycloheptanepropionyl. Cyclohexanecarbonyl is especially preferred.

When the acyl group is pyridinecarbonyl, there are included picolinoyl (2-pyridinecarbonyl), nicotinoyl (3-pyridinecarbonyl) and isonicotinoyl (4-pyridinecarbonyl).

When the acyl group is

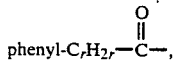

there are included, for example, benzoyl, phenylacetyl, α-phenylpropionyl, β-phenylpropionyl, p-toluyl, m-toluyl, o-toluyl, o-ethylbenzoyl, p-tert-butylbenzoyl, 3,4-dimethylbenzoyl, 2-methyl-4-ethylbenzoyl, 2,4,6-trimethylbenzoyl, m-methylphenylacetyl, p-isobutylphenylacetyl, β-(p-ethylphenyl)propionyl, p-anisoyl, m-anisoyl, o-anisoyl, m-isopropoxybenzoyl, p-methoxyphenylacetyl, m-isobutoxyphenylacetyl, m-diethylaminobenzoyl, 3-methoxy-4-ethoxybenzoyl, 3,4,5-trimethoxybenzoyl, p-dibutylaminobenzoyl, 3,4-diethoxyphenylacetyl, β-(3,4,5-trimethoxyphenyl)propionyl, o-iodobenzoyl, m-bromobenzoyl, p-chlorobenzoyl, p-fluorobenzoyl, 2-bromo-4-chlorobenzoyl, 2,4,6-trichlorobenzoyl, p-chlorophenylacetyl, α-(m-bromophenyl)propionyl, p-trifluoromethylbenzoyl, 2,4-di(trifluoromethyl)-benzoyl, m-trifluoromethylphenylacetyl, β-(3-methyl-4-chlorophenyl)propionyl, p-dimethylaminobenzoyl, p-(N-methyl-N-ethylamino)benzoyl, o-acetamidobenzoyl, m-propionamidobenzoyl, 3-chloro-4-acetamidophenylacetyl, p-n-butoxybenzoyl, 2,4,6-triethoxybenzoyl, β-(p-trifluoromethylphenyl)-propionyl, 2-methyl-4-methoxybenzoyl, p-acetamidophenylpropionyl, and 3-chloro-4-ethoxybenzoyl.

When the hydroxyl protective group is a carbonate grouping, it has the structural formula

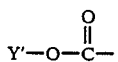

i.e., it is an organic radical which can be considered to be derived from a carbonic acid by removal of the hydroxyl group from the COOH portion. Y' preferably represents alkyl having 1 to 7 carbon atoms; alkenyl having one or two double bonds and 2 to 7 carbon atoms;

wherein the cycloalkyl portion contains 3 to 7 ring atoms and r is zero, one, two or three; phenoxy; 2-, 3-, or 4-pyridyl; or

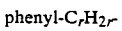

wherein r is zero, one, two or three and phenyl is unsubstituted or is substituted by 1 to 3 alkyl each having 1 to 4 carbon atoms, alkoxy having 1 to 4 carbon atoms, halo, trifluoromethyl, dialkylamino having 2 to 8 carbon atoms or alkanoylamino having 2 to 6 carbon atoms. Most preferably, Y' is $C_1$–$C_7$ alkyl, particularly ethyl or isopropyl.

Similarly, the expression "carboxyl protective group" as used hereinbelow is intended to designate a group which is inserted in place of the hydrogen atom(s) of a COOH group or groups in order to prevent premature metabolism of said COOH group or groups prior to the compound's reaching the desire site in the body. Typical carboxyl protective groups are the groups encompassed by Y' above, especially $C_1$–$C_7$ alkyl, particularly ethyl, isopropyl and t-butyl. While such simple alkyl esters and the like are often useful, other carboxyl protecting groups may be selected in order to achieve greater control over the rate of in vivo hydrolysis of the ester back to the acid and thus enhance drug delivery. To that end, carboxyl protecting groups such as the following may be used to replace the hydrogen of the —COOH group:

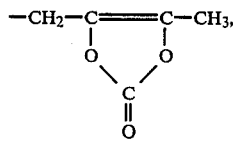

-alk-OC-alkyl,

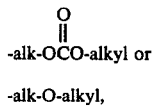
-alk-OCO-alkyl or

-alk-O-alkyl, wherein alk is $C_1$–$C_6$ straight or branched alkylene and the alkyl radical is straight or branched and contains 1 to 7 carbon atoms (e.g.

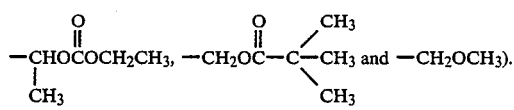

By "centrally acting primary, secondary or tertiary amine" as used herein there is intended any drug species or the like which contains a primary amino, secondary amino or tertiary amino function, a significant (usually, principal) pharmacological activity of which is CNS and a result of direct action in the brain. The term "drug" as used herein means any substance intended for use in the diagnosis, cure, mitigation, treatment or prevention of disease or in the enhancement of desirable physical or mental development and conditions in man or animal.

Exemplary such centrally acting primary amines are sympathetic stimulants and related nervous system agents, e.g., phenylethylamine (a stimulant), dopamine (a neurotransmitter and dopaminergic agent used, e.g., in the treatment of Parkinsonism or hyperprolactinemia), tyramine (a stimulant), L-DOPA (a dopamine precursor used, for example, in the treatment of Parkinsonism); narcotic analgesics; other stimulants; small peptides, such as the di-, tri-, tetra- and pentapeptides, and other small 2–20 amino acid unit containing peptides, e.g., the enkephalins (for example, Tyr-Gly-Gly-Phe-Leu), which, besides being analgesics, initiate epileptic activity in the brain at doses that are about tenfold lower than for effecting analgesic activity; larger peptides, such as pituitary hormones and related agents; growth-promoting substances; amphetamine-like drugs; anticancer and anti-Parkinsonism agents; antihypertensives; agents to enhance learning capacity and the memory processes, including treatment of dementias, such as Alzheimer's disease; antibacterials; monoamine oxidase (MAO) inhibitor drugs; CNS or brain important/essential amino acids, such as tryptophan (which is an antidepressant as well as a nutrient); and any like centrally acting primary amines.

Other illustrative ultimate species of centrally active drug entities containing a primary amino group and the classes of drugs of which they are representative are as follows: amphetamine, dextroamphetamine, levamphetamine, aletamine, cypenamine and phentermine, which are sympathomimetic amines/cerebral stimulants and appetite suppressants; etryptamine, a cerebral stimulant; anileridine, which is a narcotic analgesic; methyldopa, which is a sympatholytic agent used, e.g., in hypertension; tranylcypromine, a sympathomimetic cerebral stimulant/MAO inhibitor and antidepressant; norepinephrine, a sympathetic stimulant/adrenergic agent; hydralazine, a hypotensive; amoxicillin and ampicillin, which are penicillin-type antibiotics; guanethidine, a hypotensive/sympatholytic; GABA, γ-vinyl GABA and γ-acetylenic GABA, neurotransmitters for possible use in epilepsy; doxorubicin and daunamycin, anticancer/antitumor agents; cephalexin, a cephalosporin antibiotic; ACTH (corticotropin); LH-RH, a neurotransmitter; melphalan, a nitrogen mustard-type anticancer-/antitumor agent; DON, an anticancer urea derivative; nimustine, an anticancer/antitumor nitrosourea derivative; amiphenazole, a stimulant; debrisoquin, a hypotensive; bacampicillin and pivampicillin, which are penicillin-type antibiotics; ceforanide and cefroxadine, which are cephalosporin-type antibiotics; and 6[[(hydroxyimino)phenyl]methyl]-1-[(methylethyl)sulfonyl]-1H-benzimidazol-2-amine, an antiviral agent.

Exemplary centrally acting secondary amines in accord with this invention and the classes of drugs of which they are representative are as follows: mitoxantrone, an anticancer/antitumor agent; epinephrine, an adrenergic agent; phenylephrine, a sympathomimetic amine/decongestant; noracymethadol, a narcotic analgesic of the methadone-type; piminodine, a narcotic analgesic of the meperidine-type; tracazolate, a sedative/hypnotic; tiletamine, an anticonvulsant; propranolol, metoprolol, nadolol, timolol and atenolol, which are β-blockers; prizidilol, a centrally acting hypotensive; benzoctamine, a sedative/muscle relaxant which structurally is an analogue of the phenothiazine tranquilizers; chlordiazepoxide, a tranquilizer of the benzodiazepine-type; methamphetamine, fencamfamin, fenozolone and zylofuramine, which are sympathomimetic amines/cerebral stimulants; desipramine, nortriptyline, octriptyline, protriptyline and maprotiline, which are cerebral stimulants/tricyclic antidepressants of the dibenzazepine-type; amedalin, bupropion, cartazolate, daledalin, difluanine, fluoxetine and nisoxetine, which also are cerebral stimulants; bethanidine, a hypotensive; and ephedrine and pseudoephedrine, which are sympathomimetic amines.

Exemplary such centrally acting tertiary amines and the classes of drugs of which they are representative are as follows: methadone, levomethadyl acetate, dextromoramide, propoxyphene, carbiphene and pyrroliphine, which are narcotic analgesics of the methadone-type; phenampromide and tilidine, which are narcotic analgesics of the meperidine-type; methotrimeprazine, which is a phenothiazine analgesic; clozapine and perlapine, which are sedatives/hypnotics/anticonvulsants of the benzodiazepine-type; cloperidone, a sedative/hypnotic of the quinazolone-type; atolide, an anticonvulsant; guanethidine, a sympatholytic hypotensive; chlorpromazine, propiomazine, perphenazine, trifluoperazine, promazine, triflupromazine, acepromazine, acetophenazine, butaperazine, carphenazine, fluphenazine, prochlorperazine, thiopropazate, piperacetazine and pipotiazine palmitate, which are tranquilizers/antipsychotics of the phenothiazine-type, a number of which are also useful as sedatives (e.g. chlorpromazine, propiomazine, perphenazine and trifluoperazine); chlorprothixine, a thioxanthine calming agent which structurally is an analogue of the phenothiazine tranquilizers; thiothixine, a thioxanthine alerting agent (used, e.g., in chronic withdrawn schizophrenia) which structurally is an analogue of the phenothiazine tranquilizers; doxepin and cidoxepin, tricyclic antidepressants which structurally are dibenzoxapine analogues of the phenothiazine tranquilizers; loxapine, a tranquilizer/antipsychotic (used, e.g., in treating chronic and acute schizophrenia) which structurally is an analogue of the phenothiazine tranquilizers; clomacran, clopenthixol and clothiapine, which are antipsychotics which structurally are analogues of the phenothiazine tranquilizers; clozapine, dimeprozan, perlapine and pinoxepin, which also are analogues of the phenothiazine tranquilizers and are variously used as sedatives, hypnotics and tranquilizers; pipamperone, an antipsychotic; flurazepam, adinazolam, flumezapine and metiapine, sedatives of the benzodiazepine-type, some of which are also used as hypnotics; doxapram, a medullary stimulant; dimethazan, a xanthine-type cerebral stimulant; prolintane and thozalinone, sympathomimetic amine-type cerebral stimulants; gamfexine, a cerebral stimulant of the diphenylmethane analogue type; cyclobenzaprine, a muscle relaxant; clodazon, an antidepressant; amitriptyline, imipramine, opipramol, doxepin, cidoxepin, amoxapine, azipramine, butriptyline, clomipramine, dibenzepin, dothiepin, intriptyline, ketipramine, melitracen and trimipramine, which are tricyclic antidepressants/cerebral stimulants of the dibenzazepine-type (i.e. dibenzazepines and their analogues such as dibenzoxepines), all of which can be considered as analogues of the phenothiazine tranquilizers; and cyclindole, difluamine, fantridone, flubanilate, iprindole, modaline, pirandamine, pyrovalerone, tandamine, thiazesim, trazodone and trebenzomine, which also are cerebral stimulants.

Preferred classes of centrally acting primary, secondary and tertiary amines encompassed hereby are the central neurotransmitters, anticancer and antitumor agents, antiviral agents, memory enhancers, hypotensives, sedatives, tranquilizers, antipsychotics, narcotic analgesics and cerebral stimulants, especially preferred cerebral stimulants being the tricyclic antidepressants. Among the neurotransmitters, there can be mentioned amino acids, such as GABA, GABA derivatives and other omega-amino acids, as well as glycine, glutamic acid, tyrosine, aspartic acid and other natural amino acids; catecholamines, such as dopamine and norepinephrine; serotonin, histamine and tryptamine; and peptides such as neurotensin, luteinizing hormone-releasing hormone (LHRH), somatostatin, enkephalins such as met$^5$-enkephalin and leu$^5$-enkephalin, endorphins such as γ-, α- and β-endorphins, and vasopressin. Synthetic and semi-synthetic analogues, e.g. analogues of LHRH in which one or more amino acid(s) has/have been eliminated and/or replaced with one or more different amino acid(s), and which may be agonists or antagonists, are also contemplated, e.g. the primary and secondary amine LHRH analogues disclosed in U.S. Pat. Nos. 4,377,574, 3,917,825, 4,034,082 and 4,338,305. Among the anticancer and antitumor agents, there can be mentioned L-alanosine, DON, bactobolin, acivicin, melphalan, adriamycin (doxorubicin), daunomycin, mitoxantrone and nimustine. Among the antiviral agents, there can be mentioned amantadine (also of possible value as an anti-Parkinsonism agent); diarylamidines such as 5-amidino-2-(5-amidino-2-benzofuranyl)indole and 4',6-diimidazolino-2-phenylbenzo(b)thiophen; 2-amino-oxazoles such as 2-guanidino-4,5-di-n-propyloxazole and 2-guanidino-4,5-diphenyloxazole; benzimidazole analogues such as the syn and anti isomers of 6[[(hydroxyimino)phenyl]methyl]-1-[(1-methylethyl)sulfonyl]-1$\underline{H}$-benzimidazol-2-amine; and glycosides such as glucosamine and 6-amino-6-deoxy-D-glucose. Among the hypotensives, there can be mentioned methyldopa, debrisoquin, hydralazine, and guanethidine and its analogues. Among the sedatives, tranquilizers and antipsychotics, there can be mentioned the many specific compounds of this type already disclosed above, especially the phenothiazines and benzodiazepines and their analogues. Among the narcotic analgesics, there can be mentioned in particular the methadone-type and meperidine-type compounds specified hereinabove. Among the cerebral stimulants, there can also be mentioned the many specific compounds set forth hereinabove, particularly the sympathomimetic amine-type cerebral stimulants and the tricyclic antidepressants, especially preferred tricyclics being the dibenzazepines and dibenzoxapines and their analogues.

Also illustrative of the centrally acting drug species containing primary, secondary or tertiary amine groups contemplated by this invention are centrally active metabolites of centrally acting drugs. Such metabolites are typified by hydroxylated metabolites of tricyclic antidepressants, such as the E- and Z-isomers of 1-hydroxynortriptyline, 2-hydroxyimipramine, 2-hydroxydesipramine and 8-hydroxychloripramine; and hydroxylated metabolites of phenothiazine tranquilizers, e.g. 7-hydroxychlorpromazine. Other CNS active metabolites for use herein will be apparent to those skilled in the art. Typically, these CNS active metabolites have been identified as such in the scientific literature but have not been administered as drugs themselves. In many cases, the active metabolites are believed to be comparable in CNS activity to their parent drugs; frequently, however, the metabolites have not been administered per se because they are not themselves able to penetrate the blood-brain barrier.

As indicated hereinabove, diagnostic agents, including radiopharmaceuticals, are encompassed by the expression "centrally acting drug" or the like as used herein. Any diagnostic agent which can be derivatized to afford a compound of formula (I) which will penetrate the BBB and concentrate in the brain in its quaternary form (II) and can be detected therein is encompassed by this invention. The diagnostic may be "cold" and be detected by X-ray (e.g. radiopaque agents) or other means such as mass spectrophotometry, NMR or other non-invasive techniques (e.g. when the compound includes stable isotopes such as C 13, N 15, O 18, S 33 and S 34). The diagnostic alternatively may be "hot", i.e. radiolabeled, such as with radioactive iodine (I 123, I 125, I 131) and detected/imaged by radiation detection/imaging means. Typical radiolabeled diagnostics include diotyrosine (I 125, I 131), p-iodo-N-isopropylamphetamine (I 123), iotyrosine (I 131) and iodometaraminol (I 123), which has the structural formula

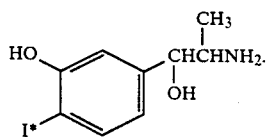

Yet other radiolabeled diagnostics include p-iodophenethylamine and p-iodobenzylamine (labeled, e.g. with I 123 or I 125). In the case of diagnostics, as in the case of drugs which are for the treatment of disease, the "locked in" quaternary form will be the form that is imaged or otherwise detected, not the original diagnostic itself. Moreover, any of the centrally acting drugs encompassed by this invention which are intended for the treatment or prevention of medical disorders but which can be radiolabeled, e.g. with a radioisotope such as iodine, or labeled with a stable isotope, can thus be converted to a diagnostic for use herein. Put another way, any compound of formula (I) of this invention which can have incorporated into its structure such a radioactive or stable isotope [either directly or through incorporation of the isotope into the structure of the corresponding compound of formula (II)] can be used for diagnostic purposes.

It will be apparent from the known structure of the many drug species exemplified above, that in many cases the selected drug will possess more than one reactive functional group, and, in particular, that the drug may contain hydroxyl or carboxyl or other functional groups in addition to the amino group or groups which is/are to be replaced with the redox system, and that these additional groups will at times benefit from being protected during synthesis and/or during administration. The nature of such protection is described in more detail below. Obviously, such protected drug species are encompassed by the definition of "drug" set forth hereinabove.

By "residue of a centrally acting primary, secondary or tertiary amine" as used herein there is meant that portion of the centrally acting amine which would remain after removal of the respective primary, secondary or tertiary amino group therefrom, e.g., in the case of phenethylamine, which has the structural formula

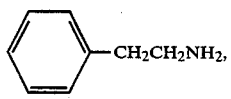

the corresponding residue would be

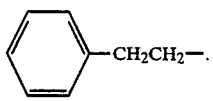

In the case of centrally acting amines which also contain one or more hydroxy groups and/or one or more carboxy functions, the residue thereof may contain one or more of those hydroxy and/or carboxy functions in protected form. Thus, for example, when the centrally acting primary amine is levodopa, which has the structural formula

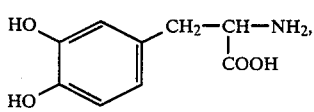

the corresponding residue would be

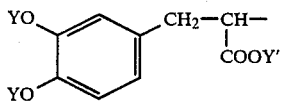

wherein each Y is hydrogen or a hydroxyl protective group as defined hereinabove (typically, acyl or carbonate) and Y' is hydrogen or a carboxyl protective group as defined hereinabove (typically, $C_1$-$C_7$ alkyl).

It will be apparent from the foregoing that different centrally acting primary, secondary and/or tertiary amines may have the same residue as defined herein and as represented by D in formulas (I) and (II). Thus, for example, desipramine, which is a tricyclic antidepressant having a secondary amine function, and imipramine, which is a tricyclic antidepressant having a tertiary amine function, both have the same residue, i.e.

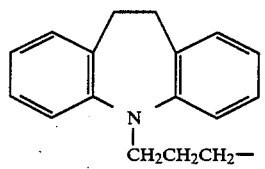

Similarly, norepinephrine and epinephrine, which are adrenergic agents and have a primary amino group and a secondary amino group, respectively, share the same residue, i.e.

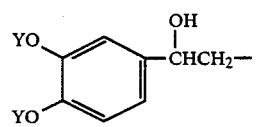

wherein each Y is defined as above. As a further example, one can mention the tertiary amine phenothiazine tranquilizers/antipsychotics, acepromazine and acetophenazine, which have the structures

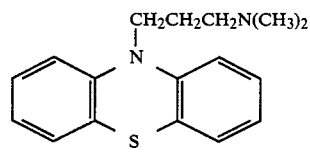

and

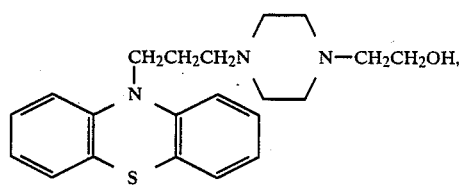

respectively, and which have the same residue, i.e.

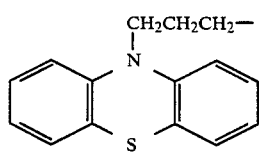

It will also be apparent from the foregoing that the exact structure of the amino function in the centrally acting amine/parent drug is immaterial insofar as concerns the structure of the instant compounds of formulas (I) and (II), for in formulas (I) and (II) the entire amino function in the parent drug has been replaced with a dihydropyridine/pyridinium salt redox system. Thus, virtually any centrally acting primary amine D-NH$_2$, secondary amine D-NHR$_1$ or tertiary amine D-NR$_2$R$_3$ can provide the drug residue D- in the instant compounds. Without being limited to specific definitions of the R$_1$, R$_2$ and R$_3$ groups in the secondary and tertiary amines, the following definitions of illustrative radicals are given:

R$_1$ can be alkyl, preferably C$_1$–C$_{10}$ alkyl; cycloalkyl, preferably C$_3$–C$_8$ cycloalkyl; alkenyl, preferably C$_2$–C$_{10}$ alkenyl; cycloalkenyl, preferably C$_3$–C$_8$ cycloalkenyl; or aryl, preferably C$_6$–C$_{10}$ aryl, particularly phenyl. Any of the foregoing R$_1$ radicals can optionally be substituted by one or more (typically 1 to 3) substituents which may be the same or different. Possible substituents on the alkyl and alkenyl radicals include C$_6$–C$_{10}$ aryl; hydroxy; hydroxy(lower alkyl)amino; substituted C$_6$–C$_{10}$ aryl wherein the substituent(s) is/are selected from the aryl substituents defined below; C$_3$–C$_8$ cycloalkyl; substituted C$_3$–C$_8$ cycloalkyl wherein the substituent(s) is/are selected from the cycloalkyl substituents defined below; halo; lower alkoxy; lower alkylthio; lower alkylsufinyl; lower alkylsulfonyl;

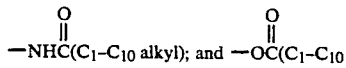

alkyl). Possible substituents on the aryl radicals include lower alkyl, halo, lower alkoxy, carbamoyl, lower alkoxycarbonyl, lower alkanoyloxy, lower haloalkyl, mono(lower alkyl)amino, di(lower alkyl)amino, mono(lower alkyl)carbamoyl, lower alkylthio, lower alkylsulfinyl and lower alkysulfonyl. Possible cycloalkyl substituents include lower alkyl; C$_6$–C$_{10}$ aryl; substituted lower alkyl wherein the substituent(s) can be any of the alkyl substituents defined above; substituted C$_6$–C$_{10}$ aryl wherein the substituent(s) can be any of the aryl substituents defined above; halo; lower alkoxy; lower alkylthio; lower alkylsulfinyl; lower alkylsulfonyl;

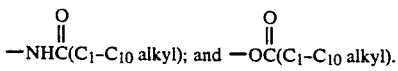

Preferred secondary amino groups —NHR$_1$ are lower alkylamino [unsubstituted or substituted by hydroxy or hydroxy(lower alkyl)amino] and phenylamino. Particularly preferred secondary amino groups include methylamino, phenylamino, tert-butylamino, isopropylamino, n-butylamino, ethylamino, 2-hydroxyethylamino and 2-(2'-hydroxyethylamino)ethylamino.

R$_2$ and R$_3$, which can be the same or different, can each be any one of the R$_1$ radicals defined above, or R$_2$ and R$_3$ can be combined such that —NR$_2$R$_3$ represents a saturated monocyclic tertiary amino group, preferably derived from a secondary amine monocycle having 5 to 7 ring atoms, optionally containing another hetero atom (—O—, —S— or —N—) in addition to the indicated nitrogen atom, and optionally bearing one or more (typically 1 to 3) substituents such as lower alkyl, substituted lower alkyl, C$_6$–C$_{10}$ aryl, substituted C$_6$–C$_{10}$ aryl, saturated monocyclic tertiary amino and carbamoyl. The substituted lower alkyl groups include alkyl groups substituted by one or more (typically 1 to 3) C$_6$–C$_{10}$ arylamino, hydroxy, C$_2$–C$_{20}$ akanoyloxy, mono(lower alkyl)carbamoyl, C$_6$–C$_{10}$ aryl or any of the other alkyl substituents defined in connection with R$_1$ above. The substituted aryl groups include aryl groups substituted by one or more (typically 1 to 3) substituents which can be halo or any of the other aryl substituents defined in connection with R$_1$ above. Illustrative of saturated monocyclic tertiary amine groups encompassed by the —NR$_2$R$_3$ term are morpholino, 1-pyrrolidinyl, 4-benzyl-1-piperazinyl, perhydro-1,2,4-oxathiazin-4-yl, 1- or 4-piperazinyl, 4-methyl-1-piperazinyl, piperidino, hexamethyleneimino, 4-phenylpiperidino, 2-methyl-1-pyrazolidinyl, 1- or 2-pyrazolidinyl, 3-methyl-1-imidazolidinyl, 1- or 3-imidazolidinyl, 4-benzylpiperidino and 4-phenyl-1-piperazinyl. Preferred tertiary amine groups encompassed by —NR$_2$R$_3$ include di(lower alkyl)amino; N-lower alkyl-N-benzylamino; N-lower alkyl-N-phenethylamino; piperidino; pyrrolidin-1-yl; piperazin-1-yl; morpholino; piperidino substituted in the 4-position by hydroxy-substituted lower alkyl, C$_2$–C$_{20}$ alkanoyloxy-substituted lower alkyl, carbamoyl or piperidino; and piperazin-1-yl substituted in the 4-position by lower alkyl, C$_2$–C$_{20}$ alkanoyloxy-substituted lower alkyl, lower monoalkylcarbamoyl-substituted lower alkyl, hydroxy-substituted lower alkyl, phenylamino-substituted lower alkyl or halophenyl. Especially preferred —NR$_2$R$_3$ groupings include dimethylamino, 4-[(2'-phenylamino)ethyl]piperazin-1-yl, piperidino, pyrrolidin-1-yl, 4- (3'-chlorophenyl)piperazin-1-yl, 4-methylpiperazin-1-yl, 4-(2'-hydroxyethyl)-piperidino, 4-[(2'-hexadecanoyloxy)ethyl]piperidino, 4-(2'-hydroxyethyl)piperazin-1-yl, 4-[2'-(N-methylcarbamoyl)ethyl]piperazin-1-yl, piperazin-1-yl, (N-benzyl-N-methyl)amino, diethylamino, morpholino, (4-carbamoyl-4-piperidino)piperidino, (N-methyl-N-phenethyl)amino and 4-(2'-acetoxyethyl)piperazin-1-yl.

The expression "non-toxic pharmaceutically acceptable salts" as used herein generally includes the non-toxic salts of compounds of formula (I) formed with nontoxic, pharmaceutically acceptable inorganic or organic acids HX. For example, the salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, fumaric, methanesulfonic, toluenesulfonic and the like. The expression "anion of a non-toxic pharmaceutically acceptable acid" as used herein, e.g. in connection with structure (II), is intended to include anions of such inorganic or organic acids HX.

It too will be appreciated that the radical represented by

in formula (I) must enable the compound of formula (I) to penetrate the BBB and must also be capable of being oxidized in vivo to the corresponding quaternary structure. The ionic entity which results from such in vivo oxidation is prevented from efflux from the brain, while elimination from the general circulation is accelerated. In contradistinction to the drug-carrier entities disclosed, for example, in *Science*, Vol 214, Dec. 18, 1981, pp. 1370–1372, however, there is no readily metabolically cleavable bond between drug and quaternary portions, and the active species delivered in the present case is not the original drug from which the compound of formula (I) was derived, but rather is the formula (II) quaternary itself.

It will also be appreciated that a compound of formula (I) may be administered as the free base or in the form of a non-toxic pharmaceutically acceptable salt thereof, i.e. a salt which can be represented by the formula

wherein D,

and HX are defined as before; and that, regardless of the actual form in which the compound is administered, it will be converted in vivo to a quaternary salt of formula (II), the anion X⁻ being present in vivo. It is not necessary that the anion be introduced as part of the compound administered. Indeed, even when the compound of formula (I) is used in its salt form, the anion of the formula (II) compound is not necessarily the same as that present in the formula (I) compound. Indeed, the exact identity of the anionic portion of the compound of formula (II) is immaterial to the in vivo transformation of (I) to (II).

In a presently preferred embodiment of the present invention, the centrally acting amine of which D is the residue is dopamine and the instant redox system is thus designed to elicit a sustained and brain-specific dopaminergic (e.g. anti-Parkinsonism or anti-hyperprolactinemia) response in the animal to which the formula (I) derivative is administered; it is believed that this effect is achieved via in vivo conversion of the formula (I) compound to the pharmacologically active formula (II) quaternary, which is essentially "locked in" the brain. In analogous fashion, the instant redox system I→ II in which D is the residue of any other centrally acting primary, secondary or tertiary amine is designed to elicit the kind of pharmacological response which would be obtained by delivery of the primary, secondary or tertiary amine itself to the brain, i.e. when the centrally acting amine/parent drug is an antitumor/anticancer agent, the instant redox system is employed to elicit an antitumor/anticancer response; when the parent drug is a sympathetic stimulant, the instant redox system is used to elicit a sympathetic stimulant or amphetamine-like response; when the parent drug is GABA or a related compound, the instant redox system is used to elicit an antiepileptic/anticonvulsant or analgesic response; when the parent drug is a tranquilizer, the instant system is used to elicit a tranquilizing response; when the parent drug is an antidepressant, the instant system is used to elicit an antidepressant response; and so forth.

With respect to the preferred embodiment referred to above, with dopamine as the parent amine, the catechol moiety thereof in certain instances being acylated, e.g. acetylated or pivalylated, and selecting

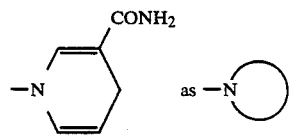

the following reaction scheme has been devised for preparation of the formula (I) analogues:

SCHEME 3

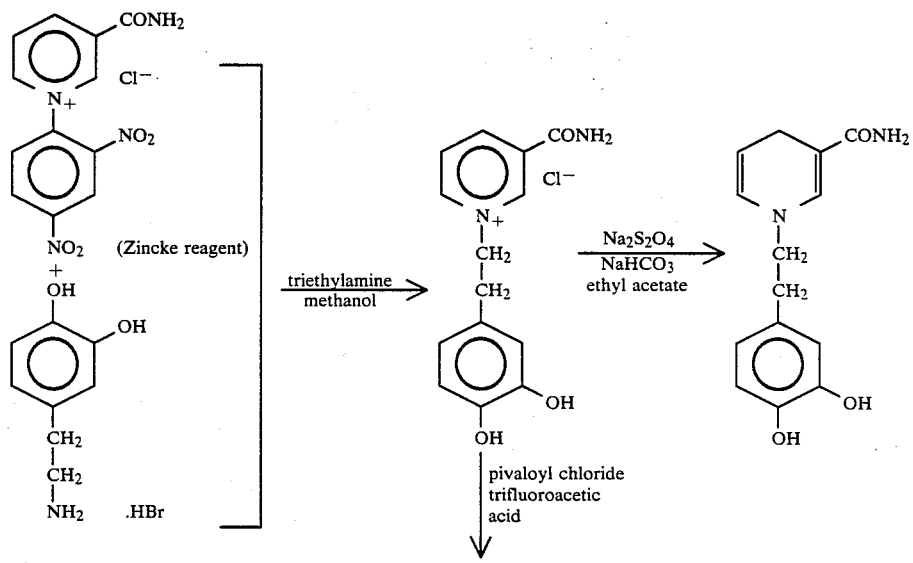

-continued
SCHEME 3
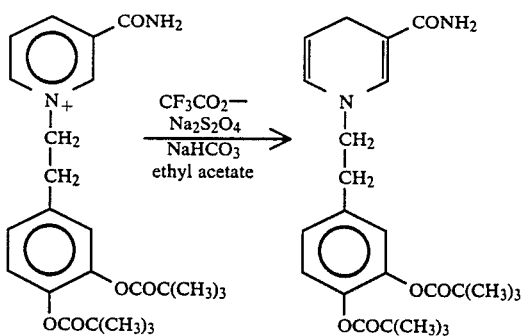
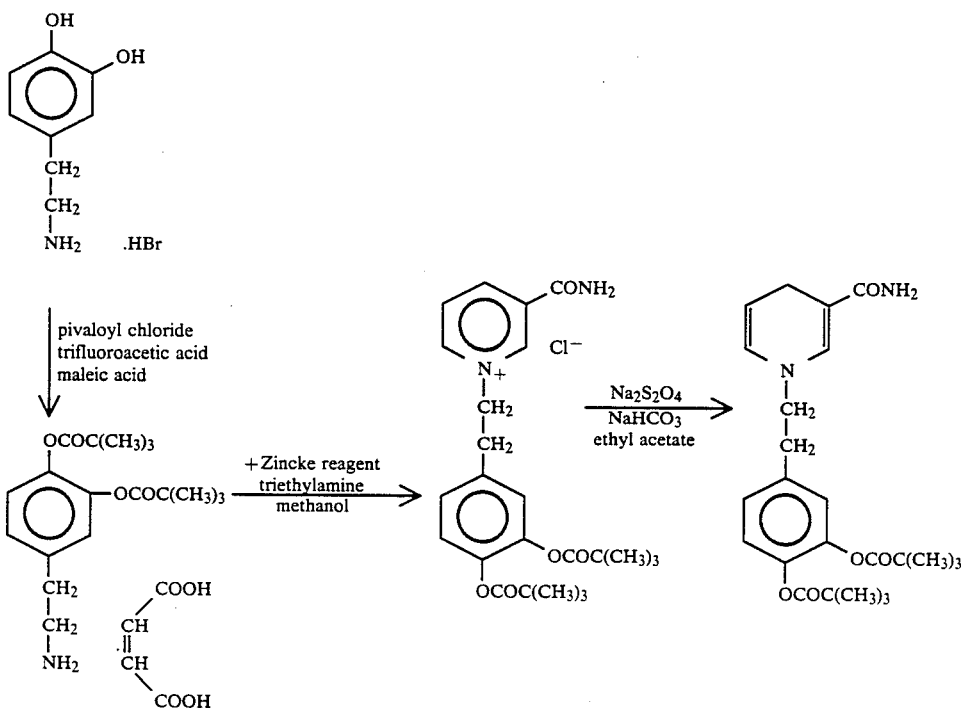
An alternate reaction Scheme for preparation of the dopamine analogues is depicted below.
SCHEME 4
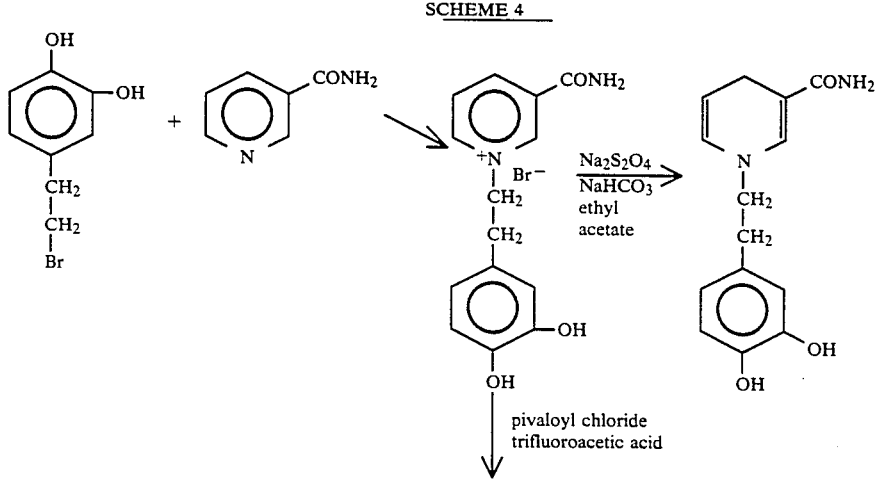

-continued
SCHEME 4

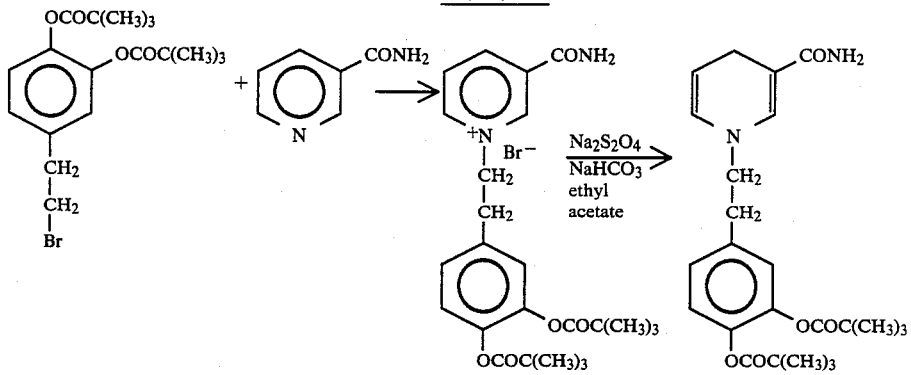

Similar schemes can be shown for the preparation of the other compounds of the invention. The acylation step, which introduces the hydroxyl protecting groups, is only needed when there are hydroxyl groups which it is desired to protect. Moreover, when carbonate rather than acyl protecting groups are desired, the step of introducing the protecting groups will involve reacting the hydroxy-containing compound with a halocarbonate of the type Y'OCOCl or Y'OCOBr (formed by reaction of Y'OH with $COCl_2$ or $COBr_2$), rather than with an acyl halide YCl or YBr, Y and Y' being as generically defined hereinabove expect that here neither Y nor Y' can be hydrogen. Also, as shown in Schemes 3 and 4, the order of steps may be altered; quaternization, followed by reduction, need not always constitute the final two steps but may be carried out earlier in the reaction sequence. Yet other reaction schemes, reactants, solvents, reaction conditions, etc. (e.g. using an anhydride rather than an acyl halide for the acylation step, or preparing a different acyl derivative, e.g. the acetyl rather than the pivalyl derivative, or using a different Zincke reagent for the exchange reaction) will be readily apparent to those skilled in the art. Also, insofar as concerns the quaternary compounds, when an anion different from the one obtained is desired, the anion in the quaternary salt may be subjected to anion exchange via an anion exchange resin or, more conveniently, by use of the method of Kaminski et al, Tetrahedron, Vol. 34, pp. 2857-2859 (1978). According to the Kaminski et al method, a methanolic solution of an HX acid will react with a quaternary ammonium halide to produce the methyl halide and the corresponding quaternary ·X salt. Moreover, the manner in which the ultimate compound is prepared should be tailored to the presence of any other reactive groups in the molecule. For example, when the parent amine contains one or more carboxy functions, such functions will typically be esterified, e.g. converted to the corresponding ethyl ester, or otherwise suitably protected, usually prior to formation of the quaternary compound. Thus, a wide variety of synthetic approaches can be utilized, depending on the desired structure of the final product.

The process exemplified in Scheme 3, i.e. reacting a starting material containing an —$NH_2$ group with a Zincke reagent, can be used to derive the instant compounds wherein D is the residue of a centrally acting primary amine directly from the corresponding centrally acting primary amine/parent drugs. However, if it is desired to prepare the instant compounds wherein D is the residue of a centrally acting secondary or tertiary amine via the process shown in Scheme 3, then one will not use the parent secondary or tertiary amine as the starting material but would instead use the corresponding primary amine as the starting material. Alternatively, a compound of the formula D-Hal wherein Hal is chloro or bromo and D is the residue of a centrally acting primary, secondary or tertiary amine can be reacted with nicotinamide or the like (as depicted in Scheme 4) to afford to desired compounds of the invention, regardless of whether the parent drug is a primary, secondary or tertiary amine.

Various illustrative synthetic schemes as applied to specific compounds of the invention are set forth below in the section entitled "Illustrative Synthetic Methods". While the sequence of reaction steps can be varied in many cases, in general the final step (except in the case of optional salt formation or possibly in the case of radiolabeling) will be reduction of a quaternary compound of formula (II) to the corresponding dihydro compound of formula (I). The reduction is usually conducted at a temperature from about $-10°$ C. to room temperature, for a period of time from about 10 minutes to 2 hours, conveniently at atmospheric pressure. Typically, a large excess of reducing agent is employed, e.g., a 1:5 molar ratio of reducing agent to starting compound of formula (II). The process is conducted in the presence of a suitable reducing agent, preferably an alkali metal dithionite such as sodium dithionite or an alkali metal borohydride such as sodium borohydride or lithium aluminum borohydride, in a suitable solvent. Sodium dithionite reduction is conveniently carried out in an aqueous solution; the dihydro product of formula (I) is usually insoluble in water and thus can be readily separated from the reaction medium. In the case of sodium borohydride reduction, an organic reaction medium is employed, e.g., a lower alkanol such as methanol, an aqueous alkanol or other protic solvent.

When a Zincke reagent is utilized in the reaction sequence, e.g. when Scheme 3 is employed, such reagent can be prepared by reacting 1-chloro-2,4-dinitrobenzene with a compound of the formula

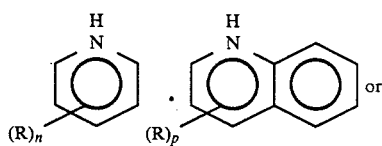

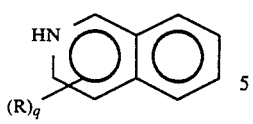

wherein R, n, p and q are defined as with formula (I), to afford the corresponding Zincke reagent of the formula

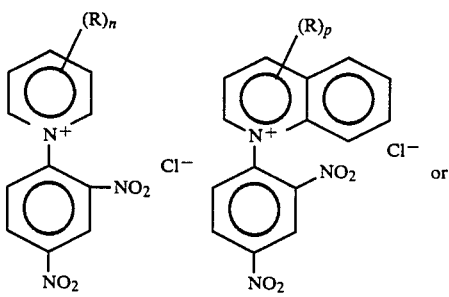

respectively. Thus, for example, the specific Zincke reagent depicted in Scheme 3 can be prepared by reacting nicotinamide with 1-chloro-2,4-dinitrobenzene. See also Zincke et al, *Annalen*, 1904, 333, 296; Lettré, *Annalen*, 1953, 579, 123; Keijzer et al, *Hetrocycles*, Vol. 16, No. 10, 1981, 1687.

In the case of radiodiagnostics, the synthetic method of choice generally involves introducing the radioactive element toward the end of the reaction sequence, rather than using the radiolabeled parent drug itself as the starting material. Schemes 5 and 6 below are illustrative of such instances of tailoring chemical synthesis to the particular drug involved. Scheme 5 depicts synthesis of an analogue of I 123 labeled metaraminol; Scheme 6 depicts a synthetic route to radioiodinated benzylamine and phenethylamine analogues.

SCHEME 5

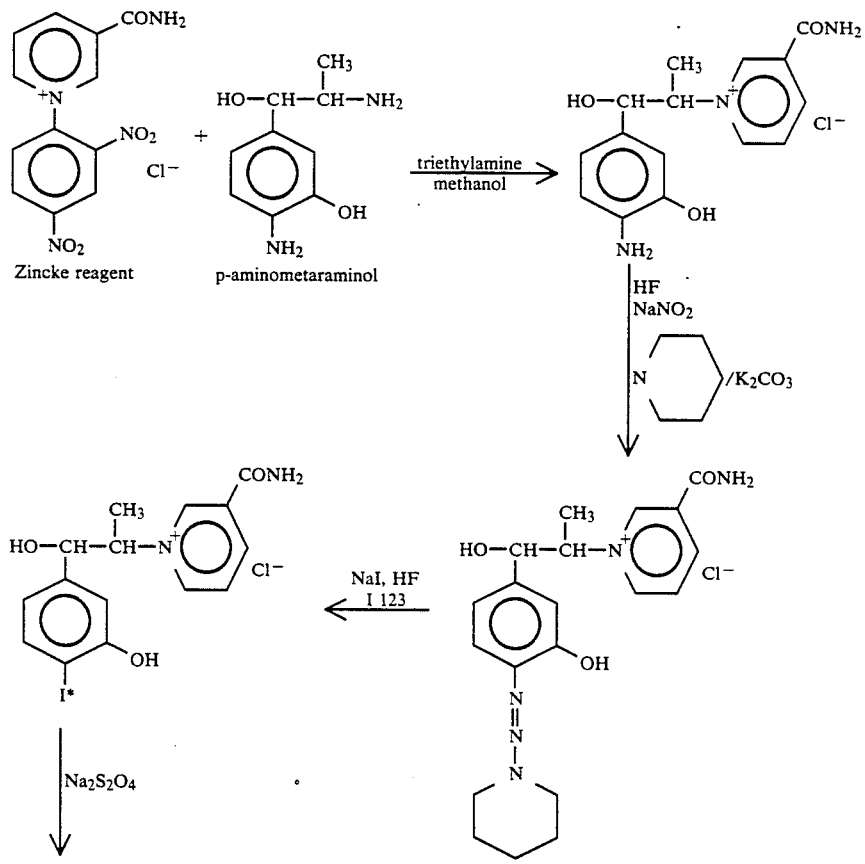

-continued
SCHEME 5

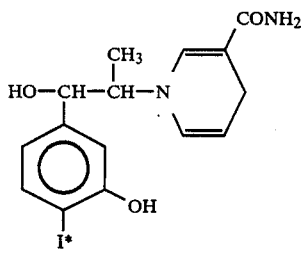

SCHEME 6

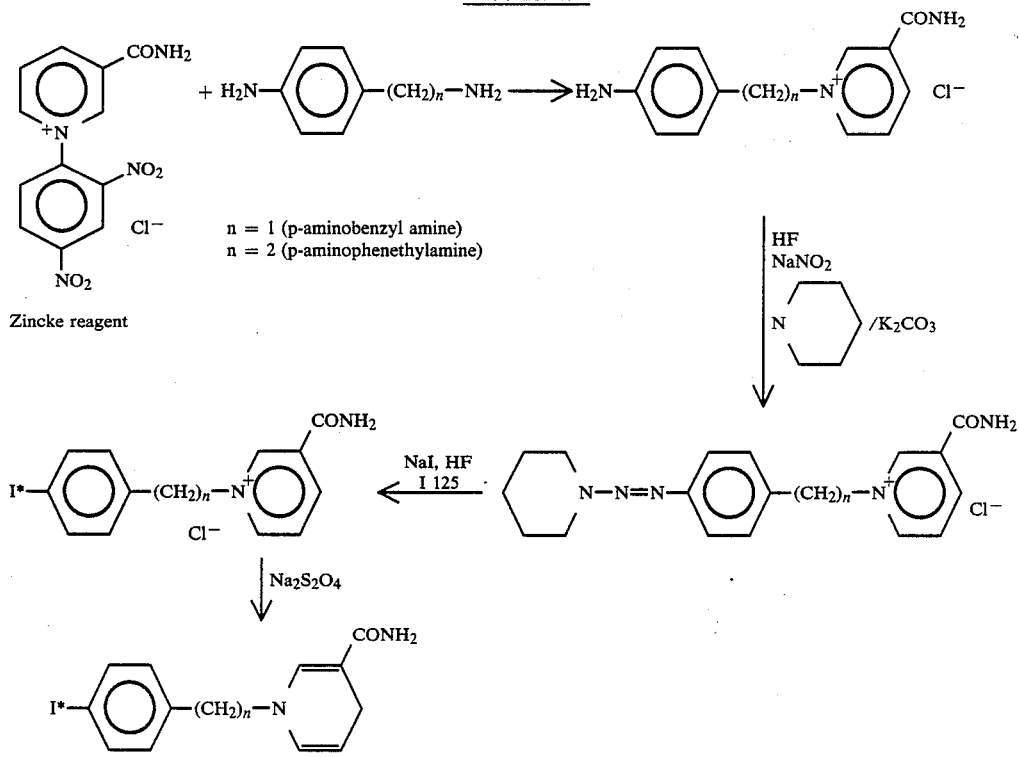

n = 1 (p-aminobenzyl amine)
n = 2 (p-aminophenethylamine)

Zincke reagent

Suitable nontoxic pharmaceutically acceptable carriers for use with the topic compounds of formula (I), e.g., those less toxic than the target drug species themselves, will be apparent to those skilled in this art. Compare, for example, Remington's Pharmaceutical Sciences, 4th Edition (1970). Obviously, the choice of suitable carriers will depend upon the exact nature of the particular dosage form selected, as well as upon the identity of the compound to be administered. The therapeutic dosage range for administration of a compound according to this invention will generally be the same as, or less than, those characteristically used in this art for administration of the known primary, secondary or tertiary amine/parent drug of which the instant compound is an analogue. Naturally, such therapeutic dosage ranges will vary with the size of the patient, the condition for which the compound is administered, the particular dosage form employed, route of administration and the like. The quantity of given dosage form needed to deliver the desired dose will of course depend upon the concentration of the compound of formula (I) in any given pharmaceutical composition/dosage form thereof. Obviously, in the case of diagnostic agents, the dosage of formula (I) compound used will be a quantity sufficient to deliver an amount of radioisotope, stable isotope or the like which can be effectively detected by radioimaging or other detection means. The amount of radioisotope, stable isotope or the like present in the dosage form will be within or below the ranges conventionally used for diagnostic purposes.

The ability of the topic compounds to cross the BBB and to be "locked into" the brain allows administration in a site-specific manner. A combination of the present dihydropyridine $\rightleftharpoons$ pyridinium salt redox system with a sustained release system will further enhance this site-specificity. Thus, a preferred embodiment of the invention comprises formulating the compound of formula (I) or its salt utilizing a sustained release carrier system and/or route of administration capable of slowly releasing the chemical, e.g., sustained release tablets and capsules for oral administration; subcutaneous injection, or implantation of drugs in solid pellet form (for example, distributed in a biodegradable polymer); intramuscular injection of the compound in solution in oil or suspended in a repository vehicle; a transdermal delivery device or form such as an ointment to be applied locally to the desired site (when the drug is susceptible of delivery through the skin), slow intravenous infusion and the like. The rate of release of compound from the sustained release system should be comparable to the rate of in vivo oxidation of the dihydro form of the redox system in order to achieve the greatest degree of enhancement of specificity.

ILLUSTRATIVE SYNTHETIC METHODS

Method A

The primary amine is reacted with the Zincke reagent of the formula

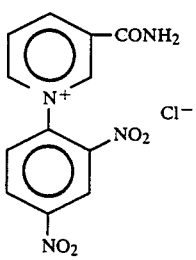

in the presence of a suitable base, e.g. triethylamine, in an appropriate organic solvent, e.g. methanol, to afford the corresponding quaternary derivative of formula (II), which is then reduced by treatment with sodium dithionite or sodium borohydride as generally described hereinabove to afford the desired compound of formula (I).

The representative primary amines listed below may be derivatized in this manner to the corresponding pyridinium and dihydropyridine analogues of this invention.

The foregoing procedure may be repeated using a Zincke reagent of the formula

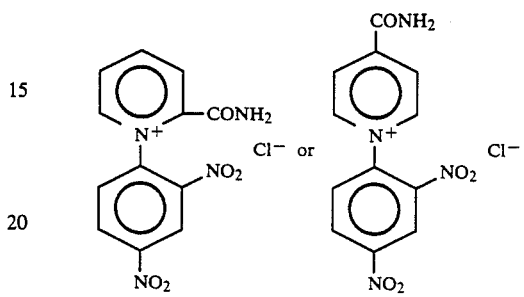

prepared from picolinamide or isonicotinamide, respectively, to convert primary amines such as those specifically mentioned in connection with this method to the corresponding quaternary and dihydro derivatives.

| STARTING MATERIAL | QUATERNARY INTERMEDIATE (CATION) | DIHYDRO DERIVATIVE |
|---|---|---|
| 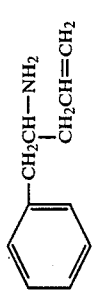<br>ALETAMINE |  |  |
| <br>CYPENAMINE |  | 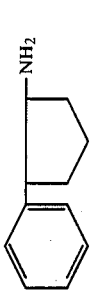 |
| 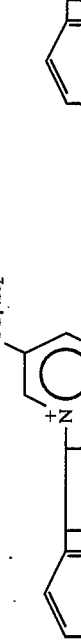<br>ETRYPTAMINE | 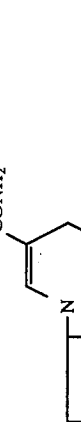 | 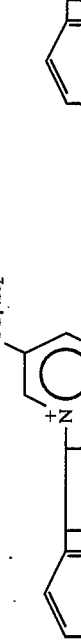 |
| 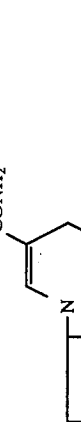<br>HYDRALAZINE | 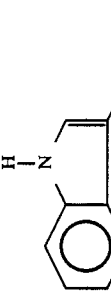 |  |

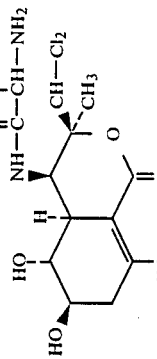

4,933,438

| STARTING MATERIAL | QUATERNARY INTERMEDIATE (CATION) | DIHYDRO DERIVATIVE |
|---|---|---|
| DAUNAMYCIN (DAUNORUBUCIN) | | |
| d-isomer DEXTROAMPHETAMINE | d-isomer | d-isomer |
| l-isomer LEVAMPHETAMINE | l-isomer | l-isomer |

| STARTING MATERIAL | QUATERNARY INTERMEDIATE (CATION) | DIHYDRO DERIVATIVE |
|---|---|---|
| DOXORUBICIN (ADRIAMYCIN) | | |
| AMPHETAMINE | | |
| PHENYLETHYLAMINE (PHENETHYLAMINE) | | |
| AMANTADINE | | |

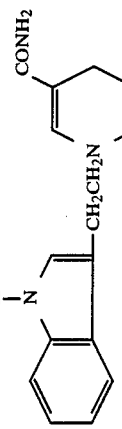

-continued

| STARTING MATERIAL | QUATERNARY INTERMEDIATE(CATION) | DIHYDRO DERIVATIVE |
|---|---|---|
| PIVAMPICILLIN | | |
| SEROTONIN | | |

Method B

This is a variation of Method A used when the parent primary amine contains a —COOH function which is to be protected.

The parent compound is first converted to the corresponding ethyl or t-butyl ester by conventional esterification techniques. That ester is then used as the starting material in Method A and that method is repeated.

Obviously, other esters may be similarly prepared in the first step by use of other esterifying agents.

The representative compounds listed below may be derivatized in this manner to the corresponding quaternary and dihydro compounds. Omega amino acids in addition to GABA (which is shown below), other natural amino acids such as glycine, aspartic acid and glutamic acid, and small peptides (2-20 amino acids, e.g. met$^5$-enkephalin and leu$^5$-enkephalin) may be similarly derivatized.

The picolinamide and isonicotinamide quaternary and dihydro derivatives of the drugs specifically mentioned for derivatizing according to this method may be similarly prepared, using the appropriate Zincke reagent. See Method A.

| STARTING MATERIAL | QUATERNARY INTERMEDIATE (CATION) | DIHYDRO DERIVATIVE |
|---|---|---|
| TRYPTOPHAN | | |
| AMPICILLIN | | |
| CEPHALEXIN | | |
| 6-AMINOPENICILLANIC ACID | | |
| MELPHALAN | | |

-continued
| STARTING MATERIAL | QUATERNARY INTERMEDIATE(CATION) | DIHYDRO DERIVATIVE |
|---|---|---|
| 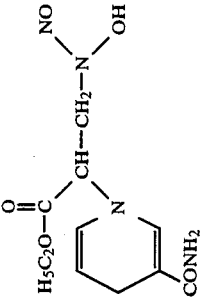 L-ALANOSINE | 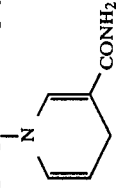 | 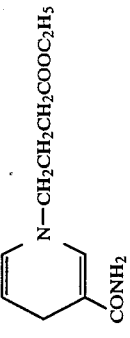 |
| 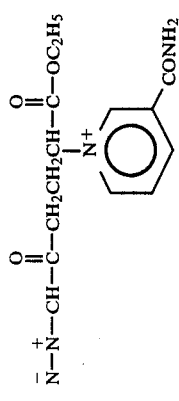 DON | 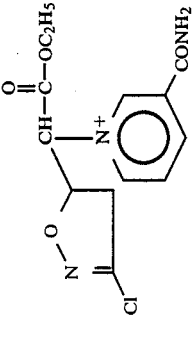 |  |
| 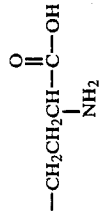 ACIVICIN | 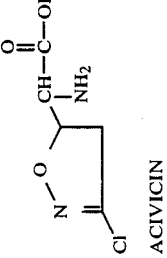 |  |
| NH₂—CH₂CH₂CH₂COOH GABA |  | 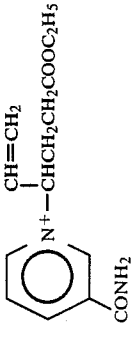 |
| 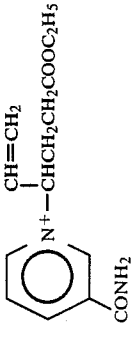 γ-VINYL GABA |  | 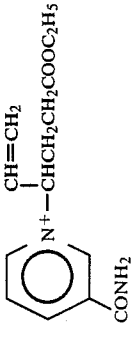 |

-continued

| STARTING MATERIAL | QUATERNARY INTERMEDIATE (CATION) | DIHYDRO DERIVATIVE |
|---|---|---|
| C≡CH<br>NH₂CHCH₂CH₂COOH<br>γ-ACETYLENIC GABA | pyridinium with CONH₂ at 3-position, N⁺-CH(C≡CH)CH₂CH₂COOC₂H₅ | 1,4-dihydropyridine with CONH₂, N-CH(C≡CH)CH₂CH₂COOC₂H₅ |
| methyldopa structure: HO,HO-C₆H₃-CH₂-C(NH₂)(CH₃)-COOH<br>METHYLDOPA | pyridinium-CONH₂, N⁺-C(CH₃)(COOC(CH₃)₃)-CH₂-C₆H₃(OH)₂ | 1,4-dihydropyridine-CONH₂, N-C(CH₃)(COOC(CH₃)₃)-CH₂-C₆H₃(OH)₂ |
| levodopa: HO,HO-C₆H₃-CH₂-CH(NH₂)-COOH<br>LEVODOPA | pyridinium-CONH₂, N⁺-CH(COOC(CH₃)₃)-CH₂-C₆H₃(OH)₂ | 1,4-dihydropyridine-CONH₂, N-CH(COOC(CH₃)₃)-CH₂-C₆H₃(OH)₂ |
| H₂N-CH(COOH)-CH₂-C₆H₄-OH<br>TYROSINE | pyridinium with CONH₂ at 3, N⁺-CH(COOC(CH₃)₃)-CH₂-C₆H₄-OH | 1,4-dihydropyridine with CONH₂, N-CH(COOC(CH₃)₃)-CH₂-C₆H₄-OH |

| STARTING MATERIAL | QUATERNARY INTERMEDIATE (CATION) | DIHYDRO DERIVATIVE |
|---|---|---|

-continued (Table of chemical structures for CEFORANIDE, CEFROXADINE, and AMOXICILLIN showing starting material, quaternary intermediate cation, and dihydro derivative forms.)

Method C

This is a variation of Method A used when the parent primary amine contains one or more OH functions which are to be protected.

The drug is first reacted with excess trimethylacetyl chloride, under strongly acid conditions, to convert the hydroxy group(s) to pivalyloxy group(s). That protected derivative is then used as the starting material in Method A and that method is repeated. Alternatively, the first two steps may be reversed, i.e., the drug may be first reacted with the Zincke reagent to form the unprotected quaternary, which may then be reacted with trimethylacetyl chloride to form the protected quaternary. The protected quaternary may then be reduced to the protected dihydro compound as in Method A.

Various other hydroxy protecting groups may be introduced in similar fashion.

The representative drugs listed below may be derivatized in this manner to the corresponding quaternary and dihydro compounds. The corresponding picolinamide and isonicotinamide quaternary and dihydro derivatives may be similarly prepared, using the appropriate Zincke reagent. See Method A.

| STARTING MATERIAL | QUATERNARY INTERMEDIATE (CATION) | DIHYDRO DERIVATIVE |
|---|---|---|
| 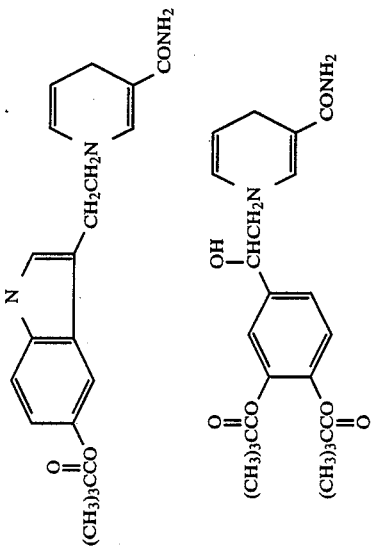 SEROTONIN | 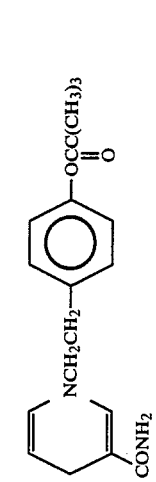 | |

Method D

This variation of Method A can be used when the drug contains one or more OH and COOH functions which are to be protected. The protecting groups, typically the ethyl or t-butyl ester and pivalyloxy groups, are introduced as described in Methods B and C, in the sequence considered most convenient. The amine function is derivatized according to Method A.

The representative drugs listed below may be derivatized in this manner to the corresponding quaternary and dihydro compounds. The corresponding picolinamide and isonicotinamide quaternary and dihydro derivatives may be similarly prepared, using the appropriate Zincke reagent. See Method A.

| STARTING MATERIAL | QUATERNARY INTERMEDIATE (CATION) | DIHYDRO DERIVATIVE |
|---|---|---|
| METHYLDOPA | | |
| LEVODOPA | | |
| TYROSINE | | |

Method E

Method A is followed, using a Zincke reagent of the formula

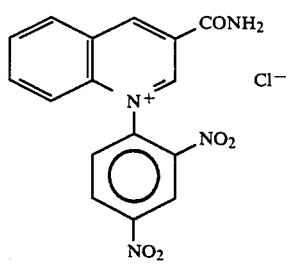

prepared from 3-quinolinecarboxamide, in place of the Zincke reagent shown in Method A.

The representative starting materials listed below may be derivatized in this manner to the corresponding quaternary and dihydro compounds, as may the remaining drugs listed with Method A.

Similarly, Method E may be combined with Methods B, C or D to afford the corresponding 3-quinoline-carboxamide derivatives, e.g. of the drugs listed with those methods.

The foregoing procedure may be repeated using a Zincke reagent of the formula

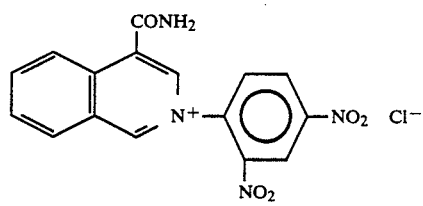

deirved from 4-isoquinolinecarboxamide, in place of the Zincke reagent shown above, to convert drugs such as those mentioned with Methods A, B, C, or D to the corresponding 4-isoquinolinecarboxamide derivatives.

The general procedures depicted above may be utilized to provide the 1,2-dihydro derivatives as well as the depicted 1,4-dihydros.

| STARTING MATERIAL | QUATERNARY INTERMEDIATE(CATION) | DIHYDRO DERIVATIVE |
|---|---|---|
| TRANYLCYPROMINE | | |
| AMANTADINE | | |
| AMPHETAMINE | | |
| PHENYLETHYLAMINE | | |

| STARTING MATERIAL | QUATERNARY INTERMEDIATE(CATION) | DIHYDRO DERIVATIVE |
|---|---|---|
| 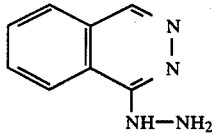 HYDRALAZINE | 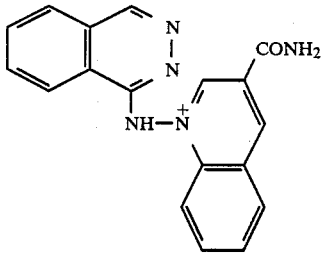 | 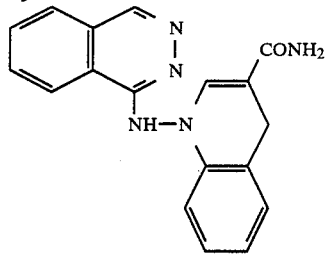 |
| 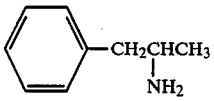 d-isomer DEXTROAMPHETAMINE | 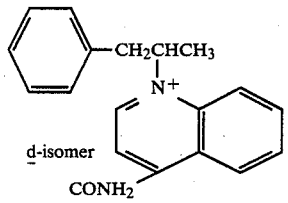 d-isomer | 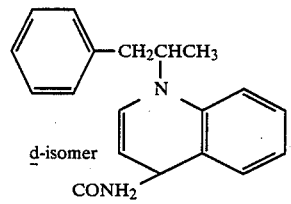 d-isomer |
| 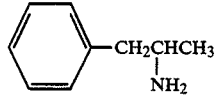 l-isomer LEVAMPHETAMINE | 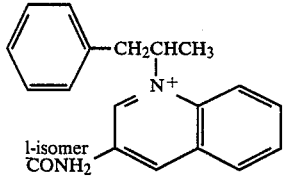 l-isomer | 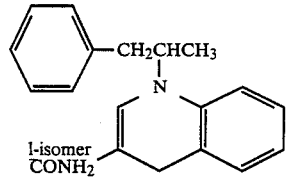 l-isomer |
| 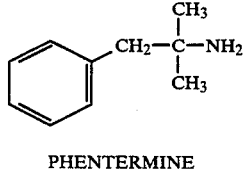 PHENTERMINE | 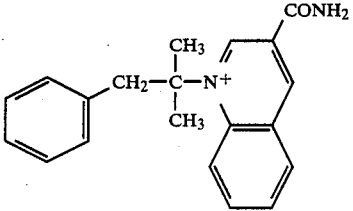 | 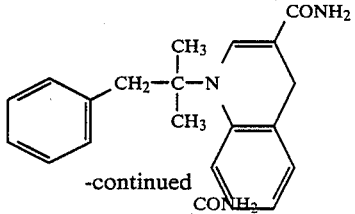 |

-continued

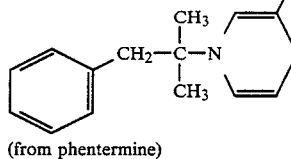
(from phentermine)

Method F

An ether solution of a compound of formula (I) is treated with an equivalent amount of anhydrous p-toluenesulfonic acid and dissolved in dry ether. Mixing at room temperature is continued until the imminium salt precipitates out of solution. The salt is then removed by filtration.

Imminium salts which may be prepared in this manner include those derived from the following compounds of the invention:

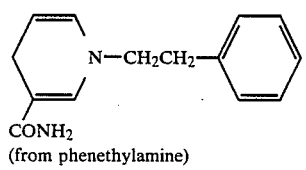
(from phenethylamine)

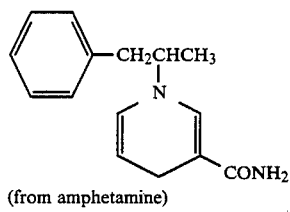
(from amphetamine)

Method G

The compounds of formulas (I) and (II) corresponding to the secondary amines/parent drugs listed below are prepared by selecting the corresponding primary amines as the starting materials and following Method C described hereinabove. Thus, the hydroxy groups are first protected, the protected primary amines are then reacted with the Zincke reagent to afford the quaternary derivatives and the quaternaries are then reduced to afford the desired compounds of formula (I).

Different protecting groups from those shown may be introduced in a similar manner.

The picolinamide and isonicotinamide quaternary and dihydro derivatives corresponding to the depicted nicotinamide derivatives may be similarly prepared, using the appropriate Zincke reagents, as described in Method A.

Method E described hereinabove may be combined with Method G to afford the corresponding 3-quinoline-carboxamide and 4-isoquinolinecarboxamide derivatives, e.g. of the parent drugs listed with this method.

| PARENT DRUG | STARTING MATERIAL | QUATERNARY INTERMEDIATE(CATION) | DIHYDRO DERIVATIVE |
|---|---|---|---|
| EPINEPHRINE | | | |
| PHENYLEPHRINE | | | |

Method H

The compounds of formulas (I) and (II) corresponding to the secondary and tertiary amines/parent drugs listed below are prepared by selecting the corresponding compounds of the formula D-Hal as the starting materials, reacting those starting materials with nicotinamide to afford the quaternary intermediates and then reducing the quaternaries with $Na_2S_2O_4$ to afford the desired dihydro derivatives.

The foregoing procedure may be repeated using picolinamide, isonicotinamide, 3-quinolinecarboxamide or 4-quinolinecarboxamide in place of the compounds of formulas (I) and (II) corresponding to parent drugs such as those specifically mentioned below.

When the parent secondary and tertiary amines contain OH and/or COOH groups in need of protection, suitable protecting groups can be introduced before or after formation of the quaternary derivatives. See, for example, Scheme 4 and Methods B, C and D hereinabove.

Method H can also be employed to prepare the compounds of formulas (I) and (II) corresponding to the primary amines listed in Methods A through E; see, for example, Scheme 4.

| PARENT DRUG | STARTING MATERIAL | QUATERNARY INTERMEDIATE (CATION) | DIHYDRO DERIVATIVE |
|---|---|---|---|
| CHLORDIAZEPOXIDE | | | |
| METHAMPHETAMINE | | | |
| PROTRIPTYLINE | | | |
| NORACYMETHADOL | | | |
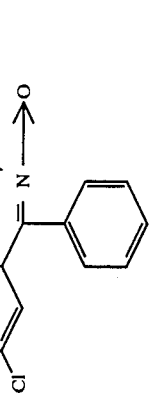

-continued

| PARENT DRUG | STARTING MATERIAL | QUATERNARY INTERMEDIATE(CATION) | DIHYDRO DERIVATIVE |
|---|---|---|---|
| PIMINODINE | | | |
| TIMOLOL | | | |
| ATENOLOL | | | |

-continued

| PARENT DRUG | STARTING MATERIAL | QUATERNARY INTERMEDIATE(CATION) | DIHYDRO DERIVATIVE |
|---|---|---|---|
| BENZOCTAMINE | | | |
| MAPROTILINE | | | |
| OCTRIPTYLINE | | | |
| AMEDALIN | | | |

-continued

| PARENT DRUG | STARTING MATERIAL | QUATERNARY INTERMEDIATE (CATION) | DIHYDRO DERIVATIVE |
|---|---|---|---|
| BUPROPION | | | |
| CARTAZOLATE | | | |
| CHLORBENZOCTAMINE | | | |
| TILETAMINE | | | |

| PARENT DRUG | STARTING MATERIAL | QUATERNARY INTERMEDIATE(CATION) | DIHYDRO DERIVATIVE |
|---|---|---|---|
| FLUOXETINE | | | |
| NISOXETINE | | | |
| TRACAZOLATE | | | |
| PROPRANOLOL | | | |

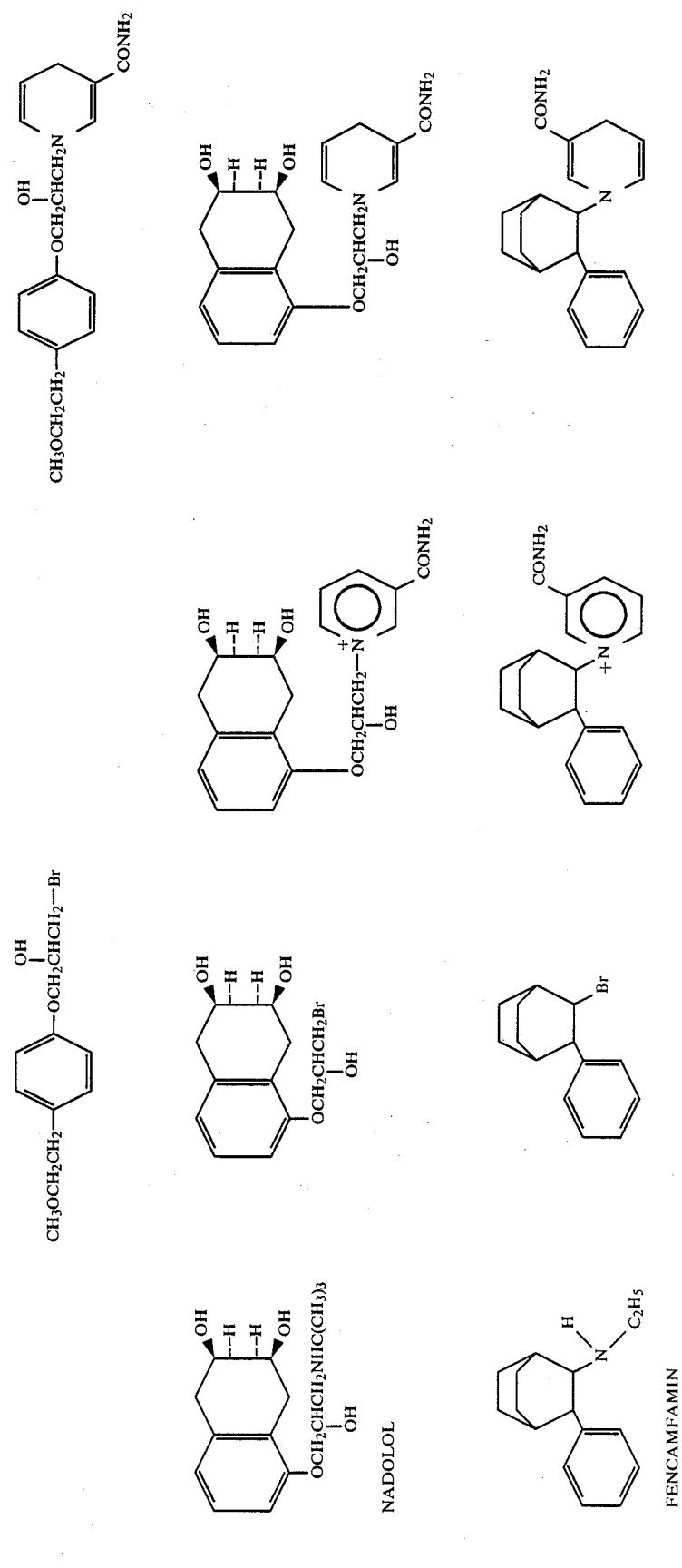

| PARENT DRUG | STARTING MATERIAL | QUATERNARY INTERMEDIATE(CATION) | DIHYDRO DERIVATIVE |
|---|---|---|---|
| 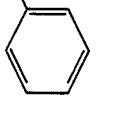 FENZOLONE | 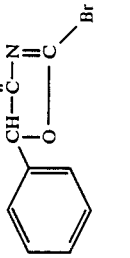 | 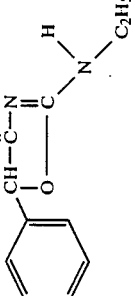 | 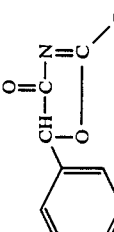 |
| 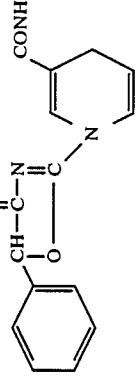 ZYLOFURAMINE | 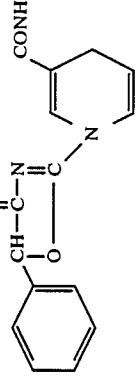 | 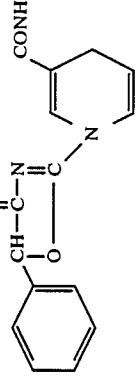 | 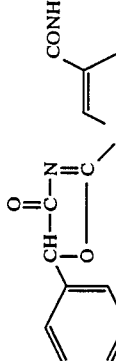 |
| 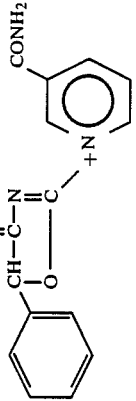 DESIPRAMINE | 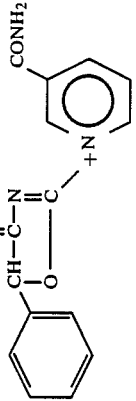 | 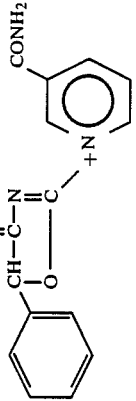 | 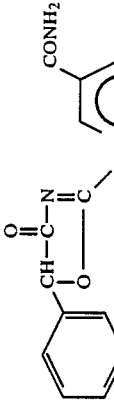 |
| 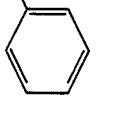 NORTRIPTYLINE | 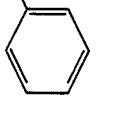 | 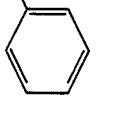 | 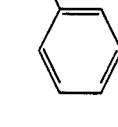 |

| PARENT DRUG | STARTING MATERIAL | QUATERNARY INTERMEDIATE (CATION) | DIHYDRO DERIVATIVE |
|---|---|---|---|
| DALEDALIN | | | |
| CLOMIPRAMINE | | | |

| PARENT DRUG | STARTING MATERIAL | QUATERNARY INTERMEDIATE(CATION) | DIHYDRO DERIVATIVE |
|---|---|---|---|

DIBENZEPIN

DOTHIEPIN

| PARENT DRUG | STARTING MATERIAL | QUATERNARY INTERMEDIATE(CATION) | DIHYDRO DERIVATIVE |
|---|---|---|---|
| INTRIPTYLINE | | | |
| KETIPRAMINE | | | |
| MELITRACEN | | | |
| TRIMIPRAMINE | | | |

| PARENT DRUG | STARTING MATERIAL | QUATERNARY INTERMEDIATE (CATION) | DIHYDRO DERIVATIVE |
|---|---|---|---|
| CYCLINDOLE | | | |
| FANTRIDOKE | | | |
| FLUBANILATE | | | |
| CHLORPROMEZINE | | | |

| PARENT DRUG | STARTING MATERIAL | QUATERNARY INTERMEDIATE (CATION) | DIHYDRO DERIVATIVE |
|---|---|---|---|
| PROMAZINE | | | |
| MITOXANTRONE | | | |

| PARENT DRUG | STARTING MATERIAL | QUATERNARY INTERMEDIATE (CATION) | DIHYDRO DERIVATIVE |
|---|---|---|---|

(table continued — chemical structures for DIFLUAMINE, TRIFLUPROMAZINE, PROPIOMAZINE, ACEPROMAZINE)

| PARENT DRUG | STARTING MATERIAL | QUATERNARY INTERMEDIATE(CATION) | DIHYDRO DERIVATIVE |
|---|---|---|---|
| DIMEPROZAN | | | |
| PERLAPINE | | | |
| PINOXEPIN | | | |
| PROLINTANE | | | |

-continued

| PARENT DRUG | STARTING MATERIAL | QUATERNARY INTERMEDIATE (CATION) | DIHYDRO DERIVATIVE |
|---|---|---|---|
| THOZALINONE | | | |
| GAMFEXINE | | | |
| AMITRIPTYLINE | | | |

4,933,438

101 102

-continued

| PARENT DRUG | STARTING MATERIAL | QUATERNARY INTERMEDIATE(CATION) | DIHYDRO DERIVATIVE |
|---|---|---|---|
| CYCLOBENZAPRINE | | | |
| IMIPRAMINE | | | |
| AMOXAPINE | | | |
| AZIPRAMINE | | | |

| PARENT DRUG | STARTING MATERIAL | QUATERNARY INTERMEDIATE(CATION) | DIHYDRO DERIVATIVE |
|---|---|---|---|
| BUTRIPTYLINE | | | |
| ACETOPHENAZINE | | | |
| CLOTHIXAMIDE | | | |

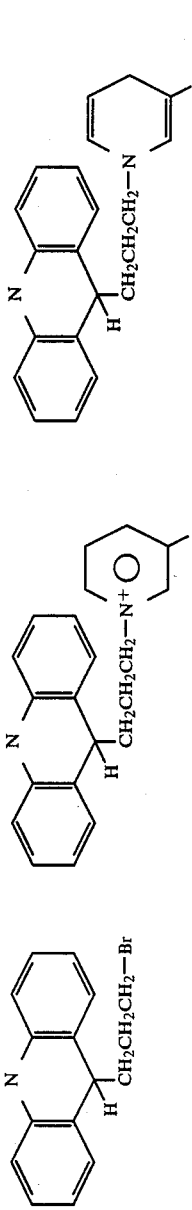

| PARENT DRUG | STARTING MATERIAL | QUATERNARY INTERMEDIATE (CATION) | DIHYDRO DERIVATIVE |
|---|---|---|---|
| TANDAMINE | | | |
| THIAZESIM | | | |
| DOXEPIN | | | |

| PARENT DRUG | STARTING MATERIAL | QUATERNARY INTERMEDIATE (CATION) | DIHYDRO DERIVATIVE |
|---|---|---|---|
| LOXAPINE | | | |
| CIDOXEPIN | | | |
| TRAZODONE | | | |

| PARENT DRUG | STARTING MATERIAL | QUATERNARY INTERMEDIATE (CATION) | DIHYDRO DERIVATIVE |
|---|---|---|---|
| OPIPRAMOL | | | |
| MODALINE | | | |
| PIRANDAMINE | | | |

| PARENT DRUG | STARTING MATERIAL | QUATERNARY INTERMEDIATE (CATION) | DIHYDRO DERIVATIVE |
|---|---|---|---|
| CLADAZON | | | |
| CARBIPHENE | | | |
| PIPAMPERONE | | | |

| PARENT DRUG | STARTING MATERIAL | QUATERNARY INTERMEDIATE (CATION) | DIHYDRO DERIVATIVE |
|---|---|---|---|

(Table contents are chemical structure diagrams for CLOPERIDONE, ADINAZOLAN, and FLUMEZAPINE.)

| PARENT DRUG | STARTING MATERIAL | QUATERNARY INTERMEDIATE(CATION) | DIHYDRO DERIVATIVE |
|---|---|---|---|
| PHENAMPROMIDE | | | |
| TILIDINE | | | |
| METHOTRIMEPRAZINE | | | |

4,933,438

| PARENT DRUG | STARTING MATERIAL | QUATERNARY INTERMEDIATE (CATION) | DIHYDRO DERIVATIVE |
|---|---|---|---|
| CLOZAPINE | | | |
| PERLAPINE | | | |
| FLURAZEPAM | | | |

-continued
| PARENT DRUG | STARTING MATERIAL | QUATERNARY INTERMEDIATE(CATION) | DIHYDRO DERIVATIVE |
|---|---|---|---|
| 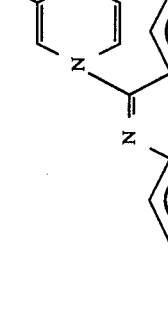<br>METIAPINE | 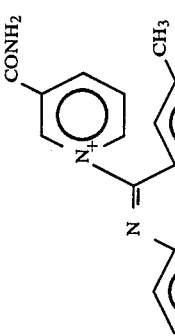 | 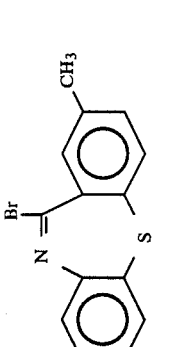 | 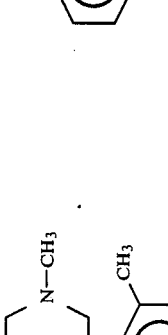 |
| 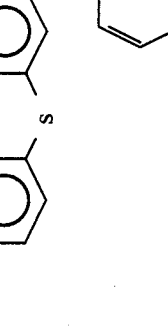<br>DOXAPRAM | 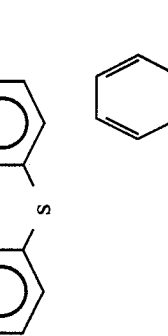 | 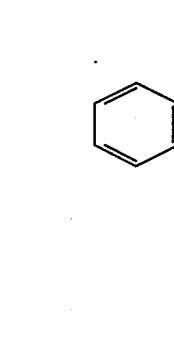 |  |

| PARENT DRUG | STARTING MATERIAL | QUATERNARY INTERMEDIATE (CATION) | DIHYDRO DERIVATIVE |
|---|---|---|---|
| DEXTROMORAMIDE | | | |
| PROPOXYPHENE | | | |
| PYRROLIPHINE | | | |

| PARENT DRUG | STARTING MATERIAL | QUATERNARY INTERMEDIATE (CATION) | DIHYDRO DERIVATIVE |
|---|---|---|---|
| THIOPROPAZATE | | | |
| METHADONE | | | |

| PARENT DRUG | STARTING MATERIAL | QUATERNARY INTERMEDIATE(CATION) | DIHYDRO DERIVATIVE |
|---|---|---|---|
| LEVOMETHADYL ACETATE | | | |
| PROCHLORPERAZINE | | | |

-continued

| PARENT DRUG | STARTING MATERIAL | QUATERNARY INTERMEDIATE (CATION) | DIHYDRO DERIVATIVE |
|---|---|---|---|
| PERPHENAZINE | | | |
| FLUPHENAZINE | | | |

-continued
| PARENT DRUG | STARTING MATERIAL | QUATERNARY INTERMEDIATE (CATION) | DIHYDRO DERIVATIVE |
|---|---|---|---|
| | 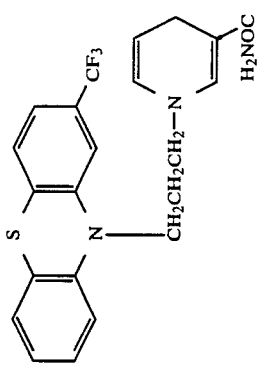 | | 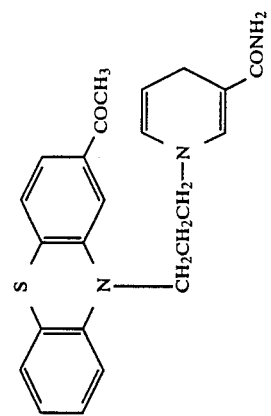 |
| | | 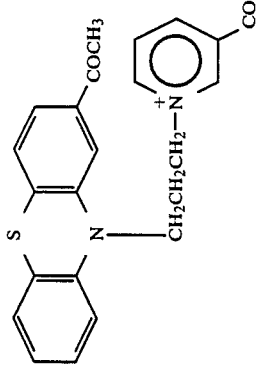 | |
| 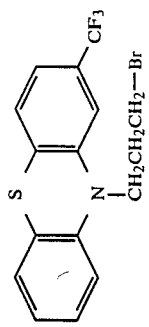 PIPERACETAZINE | 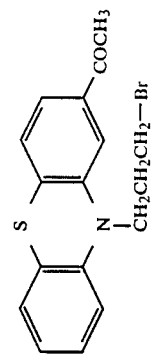 | | 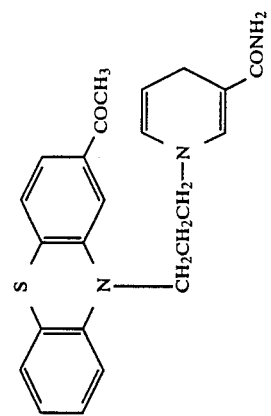 |
131 132

| PARENT DRUG | STARTING MATERIAL | QUATERNARY INTERMEDIATE (CATION) | DIHYDRO DERIVATIVE |
|---|---|---|---|

(table contains chemical structures for PIPOTIAZINE PALMITATE, TREBENZOMINE, and IPRINDOLE)

| PARENT DRUG | STARTING MATERIAL | QUATERNARY INTERMEDIATE (CATION) | DIHYDRO DERIVATIVE |
|---|---|---|---|
| TRIFLUOPERAZINE | | | |
| CHLORPROTHIXINE | | | |

| PARENT DRUG | STARTING MATERIAL | QUATERNARY INTERMEDIATE(CATION) | DIHYDRO DERIVATIVE |
|---|---|---|---|
| THIOTHIXINE | | | |
| DIMETHAZAN | | | |
| BUTAPERAZINE | | | |

| PARENT DRUG | STARTING MATERIAL | QUATERNARY INTERMEDIATE (CATION) | DIHYDRO DERIVATIVE |
|---|---|---|---|

-continued

In order to further illustrate the present invention and the advantages thereof, the following specific examples are given, it being understood that same are intended as illustrative and in nowise limitative.

EXAMPLE 1

Preparation of 1-(3,4-Dihydroxy)phenethyl-3-carbamoylpyridinium Chloride

The Zincke reagent, 1-(2,4-dinitro)phenyl-3-carbamoylpyridinium chloride (3.56 g, 0.01 mole), in methanol (10 ml), is added over a 10 minute period to a mixture of dopamine hydrobromide (2.34 g, 0.01 mole) and triethylamine (1.4 ml, 0.01 mole) in methanol (20 ml). A deep red color is immediately observed. The reaction mixture is stirred and heated at gentle reflux. After approximately 10 minutes, the red color begins to fade and precipitation of a yellow solid commences. Forty minutes later, the yellow product is collected by filtration. Recrystallization from a mixture of methanol and ethyl ether gives a pale cream powder melting at 246°–248° C. Yield 1.9 g, 73%. The product has the structural formula

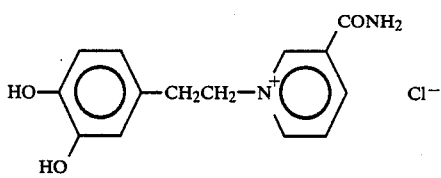

as confirmed by NMR and UV.

EXAMPLE 2

Preparation of 1-(3,4-Dihydroxy)phenethyl-3-carbamoyl-1,4-dihydropyridine 1-(3,4-Dihydroxy)phenethyl-3-carbamoylpyridinium chloride (430 mg, 15 mmol), is added to 100 ml of an ice-cold, aqueous solution of sodium bicarbonate (7.6 g, 90 mmol), sodium dithionite (13.75 g, 80 mmol) and ethyl acetate (60 ml). Nitrogen is bubbled into the mixture throughout the reaction. Addition of the pyridinium chloride starting material causes a yellow color to develop. Stirring is continued and the reaction mixture is maintained at approximately 0° C. for about one and one-half hours, after which time the ethyl acetate and aqueous layers are separated and the aqueous layer is extracted four times with 50 ml portions of ethyl acetate. The combined organic layers are dried over anhydrous magnesium sulfate and evaporated to dryness under reduced pressure. The soft yellow solid (280 mg, 75%) which remains is rapidly oxidized by methanolic silver nitrate at room temperature. Based on NMR spectra and UV and high resolution mass spectroscopy, the product is assigned the structural formula

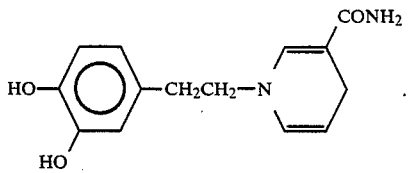

EXAMPLE 3

Preparation of 1-(3,4-Dipivaloyloxy)phenethyl-3-carbamoylpyridinium Trifluoroacetate 1-(3,4-Dihydroxy)phenethyl-3-carbamoylpyridinium chloride monohydrate (350 mg, 1.12 mmol) is dissolved in trifluoroacetic acid (5 ml) under nitrogen at room temperature. Pivaloyl chloride (0.3 ml, 24 mmol) is added dropwise to the stirred solution. Stirring is continued for one hour, after which time volatile material is removed under reduced pressure, leaving an oily residue. Extensive trituration with ethyl ether gives a fine white powder, which is collected by filtration and washed with additional ethyl ether. Yield 410 mg, 67%. The product is further characterized by the structural formula:

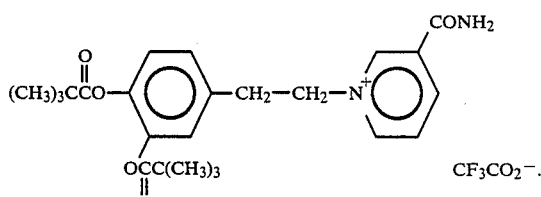

EXAMPLE 4

Preparation of 1-(3,4-Dipivaloyloxy)phenethyl-3-carbamoyl-1,4-dihydropyridine

Substitution of an equivalent quantity of 1-(3,4-dipivaloyloxy)phenethyl-3-carbamoylpyridinium trifluoroacetate for the 1-(3,4-dihydroxy)phenethyl-3-carbamoylpyridinium chloride used in Example 2 and substantial repetition of the procedure detailed in that Example affords the desired product of the formula:

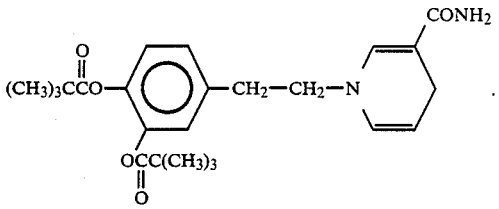

EXAMPLE 5

Preparation of (3,4-Dipivaloyloxy)phenethylamine Maleinate

Dopamine hydrobromide (11.7 g) is suspended in trifluoroacetic acid (117.5 ml) and pivaloyl chloride (13.65 ml) is added dropwise under argon. After one-half hour, water (0.75 ml) is added and solvent is evaporated under vacuum. The residue is dissolved in chloroform (200 ml) and washed, first with water, then with cold sodium bicarbonate solution, then again with water. The resultant solution is dried over anhydrous sodium sulfate and evaporated under vacuum. The residual oil is dissolved in 2-propanol (25 ml) and maleic acid (5.8 g) in warm 2-propanol (30 ml) is then added. Ethyl ether (100 ml) is added and the mixture is refrigerated at 0° C. overnight. The product is removed by filtration.

Yield 3.8 g, m.p. 146°-8° C. The product is further characterized by the structural formula:

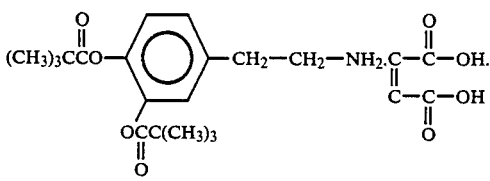

EXAMPLE 6

Preparation of 1-(3,4-Dipivaloyloxy)phenethyl-3-carbamoyl-pyridinium Chloride

Substitution of an equivalent quantity of (3,4-dipivaloyloxy)phenethylamine maleinate for the dopamine hydrobromide used in Example 1 and substantial repetition of the procedure detailed in that Example affords the desired product of the formula:

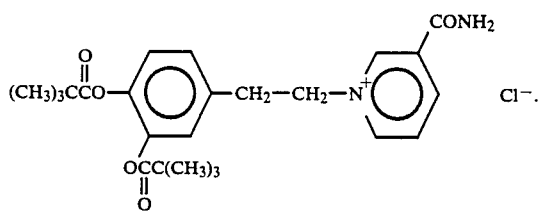

EXAMPLE 7

Preparation of 1-(3,4-Dipivaloyloxy)phenethyl-3-carbamoyl-1,4-dihydropyridine

Substitution of an equivalent quantity of 1-(3,4-dipivaloyloxy)phenethyl-3-carbamoylpyridinium chloride for the 1-(3,4-dihydroxy)phenethyl-3-carbamoylpyridinium chloride employed in Example 2 and substantial repetition of the procedure there detailed affords the desired product of the structural formula:

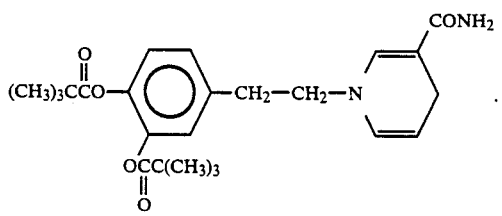

EXAMPLE 8

Preparation of 1-(2,4-Dinitro)phenyl-3-carbamoylpyridinium Chloride

1-Chloro-2,4-dinitrobenzene (20 g) is fused with nicotinamide (8 g) on a steam bath for one hour. The homogenous dark orange glassy material which results is dissolved in methanol (100 ml), with heating. Ethyl ether (400 ml) is added and a sticky yellow precipitate forms. The ether is removed, and the residue is washed again in the same way. Then, the residue is dissolved in water (200 ml), with heating. Activated charcoal is added and the mixture is refluxed for 15 minutes and filtered. A yellow glassy product, the desired Zincke reagent, forms upon evaporation of the solvent.

EXAMPLE 9

Preparation of 3-Carbamoyl-1-(3'-carboxy)propylpyridinium Chloride

The Zincke reagent prepared as in Example 8 (3.56 g, 0.01 mol) is dissolved in methanol (10 ml) and added slowly to a solution of ethyl 4-aminobutyrate hydrochloride (1.67 g, 0.01 mol) in methanol (20 ml). The deep red color of the resultant solution fades to a light orange color with stirring. The mixture is heated to a gentle boil and allowed to reflux for 30 minutes, then is stirred overnight. Crystals of dinitroaniline (10 g) are removed by filtration and the filtrate is evaporated to dryness. Recrystallization from a mixture of methanol and ethyl ether affords an orange product, which is assigned the following structure on the basis of NMR spectra and elemental analysis:

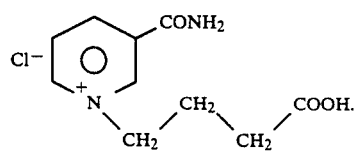

EXAMPLE 10

Preparation of 3-Carbamoyl-1-(3'-ethoxycarbonyl)propylpyridinium Chloride

The free acid product of Example 9 is suspended in ethanol. HCl gas is bubbled through the suspension at 0° C. for 45 minutes. The reaction mixture is refluxed for one hour, then allowed to cool to room temperature, producing a white precipitate. Removal of the precipitate and evaporation of the solvent produces a yellow oil, which is dissolved in a minimum amount of acetonitrile, filtered and dried. Thin layer chromatography reveals the presence of one product, which is assigned the following structure on the basis of IR, UV and NMR spectra:

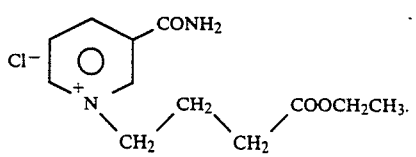

EXAMPLE 11

Preparation of 3-Carbamoyl-1-(3'-ethoxycarbonyl)propyl-1,4-dihydropyridine

3-Carbamoyl-1-(3'-ethoxycarbonyl)propylpyridinium chloride (500 mg, 1.66 mmol) is dissolved in cold deaerated water and maintained under nitrogen at 0° C. Sodium bicarbonate (0.84 g, 9.96 mmol) is added, followed by sodium dithionite (1.16 g, 6.64 mmol). Ethyl acetate is added and the mixture is stirred at 0° C., under nitrogen, for approximately one and one-half hours. Separation of the phases and drying of the organic layer affords 0.15 g (39% yield) of a yellow oil.

The following structure is assigned to the product on the basis of UV and NMR spectra:

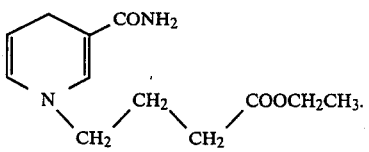

EXAMPLE 12

Preparation of 3-Carbamoyl-1-(3'-ethoxycarbonyl)propylpyridinium Bromide

Nicotinamide (7.32 g, 0.06 mol) is dissolved in dimethylformamide and ethyl 4-bromobutyrate (17.16 ml 0.12 mol) is added dropwise. The reaction mixture is brought to the reflux temperature and then maintained at that temperature for 3 hours. The solution is then allowed to cool to room temperature and stirred for 24 hours. The solvent is evaporated and the residue is washed with ethanol, separated by filtration and dried in a vacuum oven. Obtained in this manner is a white powder (6.2 g), melting at 121°–123° C. and having the structure

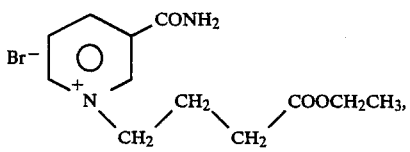

as confirmed by elemental analysis and UV, IR and NMR spectra.

EXAMPLE 13

Preparation of 3-Carbamoyl-1-(3'-ethoxycarbonyl)propyl-1,4-dihydropyridine

3-Carbamoyl-1-(3'-ethoxycarbonyl)propyl-pyridinium bromide (500 mg) is dissolved in 10 ml of deaerated ice cold aqueous ethanol (20%). Sodium bicarbonate (0.80 g) is added, followed immediately by sodium dithionite (1.10 g). Ethyl acetate is then added and the resultant yellow solution is stirred for one and one-half hours in an ice bath. Chloroform is added and the organic layer is dried over anhydrous sodium sulfate and evaporated. The resultant yellow oil is assigned the structure

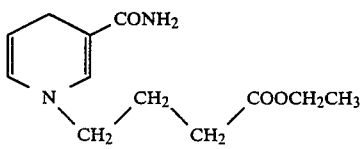

based on UV and NMR spectra and elemental analysis.

The present invention can thus be seen to provide two major classes of novel chemical compounds, i.e. the compounds of general formula (I) above, including their salts, and the compounds of general formula (II) above, wherein D is the residue of a centrally acting primary, secondary or tertiary amine and the other structural variables are as defined broadly above.

Within each of these major classes, the following subclasses are particularly noteworthy:

(A) Compounds of formulas (I) and (II) wherein the D portion of the compound of formula (I) or (II) is identical to the corresponding portion of the centrally acting amine from which D can be considered to be derived. Preferred groups of compounds in this subclass include the following:

(1) Cerebral stimulants, including sympathomimetic amine-type cerebral stimulants, such as amphetamine, dextroamphetamine, levamphetamine, aletamine, cypenamine, phentermine, methamphetamine, fencamfamin, fenozolone, zylofuramine, phenethylamine, prolintane, thozalinone, etryptamine and tranylcypromine; tricyclic antidepressant-type cerebral stimulants, especially dibenzazepines, dibenzoxepines and their analogues, e.g. desipramine, nortriptyline, protriptyline, maprotiline, octriptyline, amitriptyline, imipramine, opipramol, doxepin, cidoxepin, amoxapine, azipramine, butriptyline, clomipramine, dibenzepin, dothiepin, intriptyline, ketipramine, melitracen and trimipramine; and many other cerebral stimulants, alerting agents and antidepressants of various types, as exemplified by thiothixine, dimethazan, doxapram, gamfexine, clodazon, amedalin, bupropion, cartazolate, daledalin, cyclindole, difluanine, fantridone, flubanilate, iprindole, modaline, pirandamine, pyrovalerone, tandamine, thiazesim, amiphenazole, trazodone and trebenzomine;

(2) Anticancer or antitumor agents, e.g. daunamycin, doxorubicin, bactobolin, mitoxantrone and nimustine and the like;

(3) Antiviral agents, e.g. amantadine, 5-amidino-2-(5-amidino)-2-benzofuranyl)indole, 4',6-diimidazolino-2-phenylbenzo(b)thiophene, 2-guanidino-4,5-di-n-propyloxazole, 2-guanidino-4,5-diphenyloxazole, glucosamine, 6-amino-6-deoxy-D-glucose, 6[[(hydroxyimino)phenyl]methyl]-1-[(methylethyl)sulfonyl]-1H-benzimidazol-2-amine and the like;

(4) Neurotransmitters, e.g. tryptamine, dopamine, tyramine, somatostatin, vasopressin, serotonin and histamine;

(5) Hypotensives, including $\beta$-adrenergic blockers, e.g. propranolol, metoprolol, nadolol, timolol and atenolol; and other hypotensives, e.g. hydralazine, guanethidine, prizidilol, bethanidine and debrisoquin;

(6) Analgesics, including phenothiazine-type analgesics such as methotrimeprazine; and narcotic analgesics, particularly those of the meperidine-type, e.g. anileridine, tilidine, phenampromide and piminodine, and those of the methadone-type, e.g. methadone, levomethadyl acetate, dextromoramide, propoxyphene, carbiphene, pyrroliphine and noracymethadol;

(7) Sedatives, tranquilizers, hypnotics, antipsychotics, anticonvulsants, including benzodiazepines and their analogues, used, for example, as sedatives, hypnotics, anticonvulsants, and tranquilizers, e.g. perlapine, clozapine, flurazepam, adinazolam, flumezapine, metiapine and chlordiazepoxide; thioxanthine calming agents, e.g. chloroprothixine; muscle relaxants, e.g. cyclobenzaprine; phenothiazines and their analogues, used, for example, as tranquilizers and antipsychotics, e.g. chlorpromazine, propiomazine, perphenazine, trifluoperazine, promazine, triflupromazine, acetophenazine, butaperazine, carphenazine, fluphenazine, prochlorperazine, thiopropazate, piperacetazine, pipotiazine palmitate, acepromazine, loxapine, clomacran, clopenthixol, clothiapine, clozapine, dimeprozan, perlapine and pinoxepin; other antipsychotics, e.g. pipamperone; other sedatives and hypnotics, such as benzoctamine and tracazolate; and other anticonvulsants, such as tiletamine and atolide;

(8) LHRH and its analogues containing a primary, secondary or tertiary amino group;

(9) Antibiotics, e.g. bacampicillin, pivampicillin and the like; and

(10) Diagnostics, especially radiopharmaceuticals, such as radioiodinated p-iodometaraminol, radioiodinated p-iodobenzylamine, radioiodinated p-iodophenethylamine and radioiodinated p-iodo-N-isopropylamphetamine.

Especially preferred compounds in subclass (A) are those in which D is the residue of a compound encompassed by groups (1) and (7) above, particularly the tricyclic antidepressants.

(B) Compounds of formulas (I) and (II) wherein the centrally acting amine from which D can be considered to be derived also contains at least one —COOH functional group, and D in formula (I) or (II) contains, in place of at least one of the —COOH functional groups in said amine, at least one —COOY' group wherein Y' is a hydrolytically or metabolically cleavable carboxyl protective group. Within subclass (B), preferred compounds are those in which Y' is $C_1$–$C_7$ alkyl and/or wherein D is the residue of an amino acid (especially a naturally occurring amino acid) or of a peptide containing 2 to 20 amino acid segments, especially an enkephalin, endorphin or LHRH analogue. Specific preferred compounds of subclass (B) are those wherein D is a protected residue of a natural amino acid, such as tryptophan or tyrosine, or other amino acid/neurotransmitter such as GABA, γ-vinyl GABA or γ-acetylenic GABA; an antibiotic, e.g. a penicillin-type antibiotic, such as ampicillin, 6-aminopenicillanic acid or amoxicillin, or a cephalosporin-type antibiotic, such as cephalexin, ceforanide or cefroxadine; an anticancer/antitumor agent, e.g. a nitrogen mustard type such as melphalan, a urea type such as DON, or other anticancer/antitumor agent such as acivicin or L-alanosine; a peptide such as met$^5$-enkephalin, leu$^5$-enkephalin, γ-endorphin, α-endorphin, β-endorphin, or an endorphin, enkephalin or LHRH analogue containing a COOH group and a primary, secondary or tertiary amino group; a hypotensive, e.g. methyldopa; or a sympathetic stimulant, e.g. levodopa.

(C) Compounds of formulas (I) and (II) wherein the centrally acting amine from which D can be considered to be derived also contains at least one —OH functional group, and D in formula (I) or (II) contains, in place of at least one of the —OH functional groups in said amine, at least one —OY group wherein Y is a hydrolytically or metabolically cleavable hydroxyl protective group. Within subclass (C), preferred compounds are those wherein Y is an acyl group or a carbonate group and/or wherein D is the residue of a neurotransmitter, especially a catecholamine, or LHRH or an analogue thereof. At the present time, preferred compounds in this general class include those in which D is a protected residue of a neurotransmitter, especially a catecholamine such as dopamine, epinephrine or norepinephrine, or other neurotransmitter such as serotonin; of a structurally related compound such as phenylephrine or tyramine; or of LHRH or an LHRH analogue containing a tyrosine, serine or threonine amino acid residue (i.e., an OH-containing portion) and a primary, secondary or tertiary amino group.

(D) Compounds of formulas (I) and (II) wherein the centrally acting amine from which D can be considered to be derived also contains at least one —OH functional group and at least one —COOH functional group, and D in formula (I) or (II) contains, in place of at least one of the —OH functional groups and at least one of the —COOH functional groups in said amine, at least one —OY group and at least one —COOY' group, respectively, wherein Y is a hydrolytically or metabolically cleavable hydroxyl protective group and Y' is a hydrolytically or metabolically cleavable carboxyl protective group. Within subclass (D), preferred compounds are those wherein Y is an acyl group or a carbonate group and/or Y' is $C_1$–$C_7$ alkyl. Of particular interest are the compounds in which D is a protected residue of a hypotensive, e.g. methyldopa; a sympathetic stimulant, e.g. levodopa; a hydroxy-containing amino acid, e.g. threonine, tyrosine or serine, or a peptide containing such an amino acid, e.g. leu$^5$-enkephalin, met$^5$-enkephalin, γ-endorphin, β-endorphin, α-endorphin, other enkephalin or endorphin, or an analogue of LHRH containing a COOH group, a primary, secondary or tertiary amino function and a hydroxy-containing amino acid. Preferred peptides contain 2 to 20 amino acid segments.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A compound of the formula

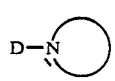

(I)

or a non-toxic pharmaceutically acceptable salt thereof, wherein D is the residue of doxorubicin or daunorubicin, said residue having the formula

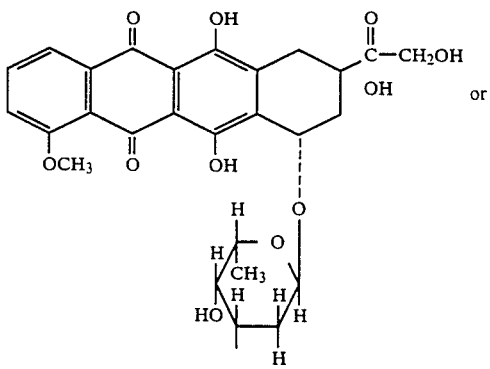

-continued

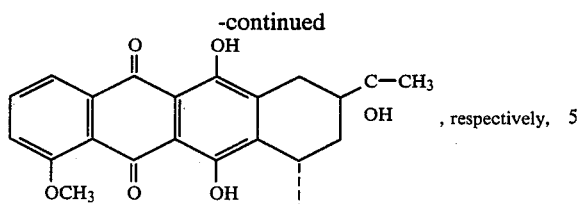
, respectively, and

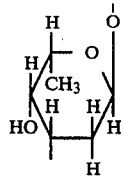

is a radical of the formula

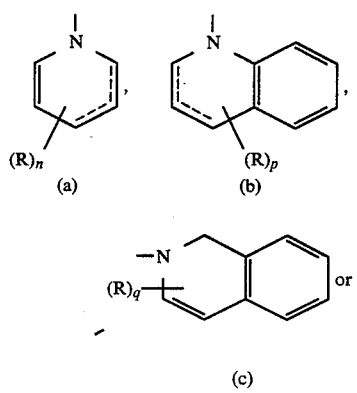

wherein the dotted line in formula (a) indicates the presence of a double bond in either the 4 or 5 position of the dihydropyridine ring; the dotted line in formula (b) indicates the presence of a double bond in either the 2 or 3 position of the dihydroquinoline ring system; m is zero or one; n is zero, one or two; p is zero, one or two, provided that when p is one or two, each R in formula (b) can be located on either of the two fused rings; q is zero, one or two, provided that when q is one or two, each R in formula (c) can be located on either of the two fused rings; and each R is independently selected from the group consisting of halo, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is H or $C_1$-$C_7$ alkyl, and —CONR'R'' wherein R' and R'', which can be the same or different, are each H or $C_1$-$C_7$ alkyl.

2. A compound according to claim 1, wherein n, m, p or q is one, and wherein R is located in the 3 position of the dihydropyridine ring, in the 3 position of the dihydroquinoline ring system or in the 4 position of the dihydroisoquinoline ring system.

3. A compound according to claim 2, wherein R is —$CONH_2$.

4. A compound according to claim 1, wherein

is a radical of the formula

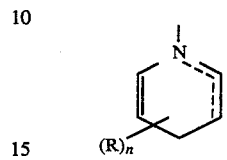

wherein the dotted line indicates the presence of a double bond in either the 4 or 5 position of the dihydropyridine ring; n is zero, one or two; and each R is independently selected from the group consisting of halo, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkythio, $C_1$—, alkylsulfinyl, $C_1$-$C_7$ alkylsulfonyl, —CH=NOR''' wherein R''' is H or $C_1$-$C_7$ alkyl, and —CONR'R'' wherein R' and R'', which can be the same or different, are each H or $C_1$-$C_7$ alkyl.

5. A compound according to claim 4, wherein n is one and R is located in the 3 position of the dihydropyridine ring.

6. A compound according to claim 5, wherein R is —$CONH_2$.

7. A compound according to claim 6, having the formula

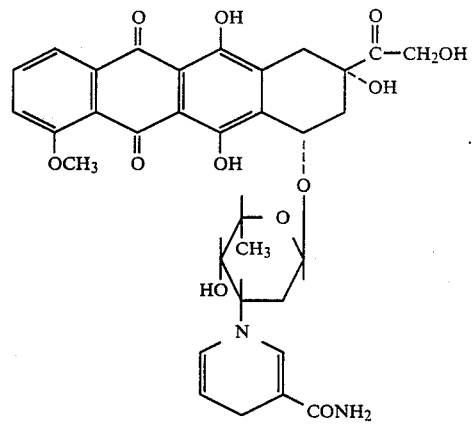

8. A non-toxic pharmaceutically acceptable quaternary salt having the formula

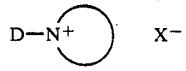

(II)

wherein D is the residue of doxorubicin or daunorubicin, said residue having the formula

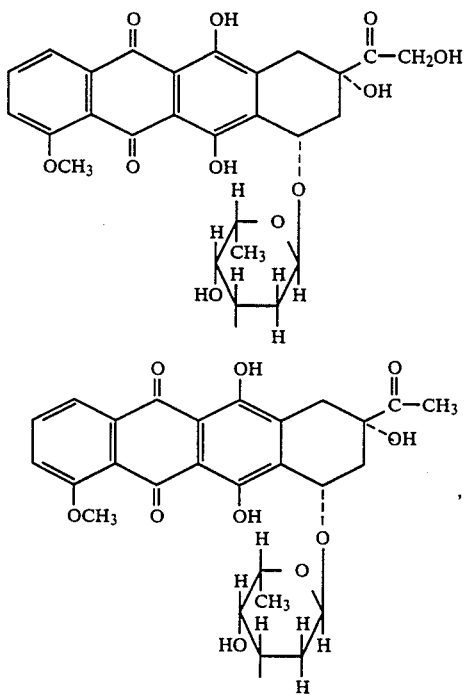

respectively, X⁻ is the anion of a non-toxic pharmaceutically acceptable acid and

is a radical of the formula

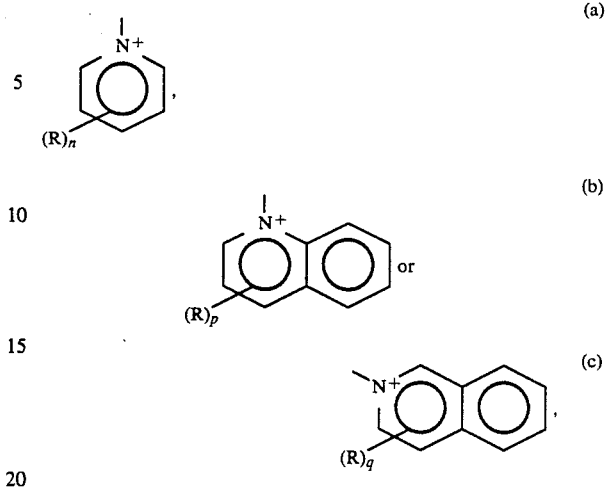

wherein n is zero, one or two; p is zero, one or two, provided that when p is one or two, each R in formula (b) can be located on either of the two fused rings; q is zero, one or two, provided that when q is one or two, each R in formula (c) can be located on either of the two fused rings; and each R is independently selected from the group consisting of halo, $C_1$-$C_7$ alkyl, $C_1$-$C_7$ alkoxy, $C_2$-$C_8$ alkoxycarbonyl, $C_2$-$C_8$ alkanoyloxy, $C_1$-$C_7$ haloalkyl, $C_1$-$C_7$ alkylthio, $C_1$-$C_7$ alkylsulfinyl, $C_1$-$C_7$ alkylsulfonyl, —CH=NOR''' wherein R''' is H or $C_1$-$C_7$ alkyl, and —CONR'R'' wherein R' and R'', which can be the same or different, are each H or $C_1$-$C_7$ alkyl.

9. A pharmaceutical composition of matter comprising an effective antitumor or anticancer amount of a compound as claimed in claim 1 and a non-toxic pharmaceutically acceptable carrier therefor.

10. A pharmaceutical composition according to claim 9, said composition being formulated as a pharmaceutically acceptable sustained release composition.

* * * * *